(12) United States Patent
Lipes et al.

(10) Patent No.: US 7,033,585 B2
(45) Date of Patent: Apr. 25, 2006

(54) IMMUNOLOGICALLY PRIVILEGED CELLS AND USES THEREOF

(75) Inventors: Myra A. Lipes, Brookline, MA (US); Qian Chen, Lowell, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 3 days.

(21) Appl. No.: 09/770,601

(22) Filed: Jan. 26, 2001

(65) Prior Publication Data

US 2002/0104110 A1  Aug. 1, 2002

Related U.S. Application Data

(62) Division of application No. 09/127,296, filed on Jul. 30, 1998, now abandoned.

(60) Provisional application No. 60/054,730, filed on Aug. 5, 1997.

(51) Int. Cl.
  *A01N 63/00* (2006.01)
  *A01N 65/00* (2006.01)
  *A61K 48/00* (2006.01)

(52) U.S. Cl. .................. 424/93.21; 424/93.1; 424/93.2

(58) Field of Classification Search ................ 435/325, 435/354, 360, 366; 424/93.1, 93.2, 93.21
See application file for complete search history.

(56) References Cited

OTHER PUBLICATIONS

Friedmann, T. (1997) Overcoming the obstacles to gene therapy. Sci. Am. Jun. 1997, pp. 96-101.*
Orkin and Motulsky (1995) Report and recommendations of the panel to assess the NIH investment in research on gene therapy.*
Verma et al. (1997) Gene therapy—promises, problems and prospects. Nature 389: 239-242.*
Halban et al. (2001) Gene and cell-replacement therapy in the treatment of type 1 diabetes. Diabetes 50: 2181-2191.*
Welsh, N. (2000) Prospects for gene therapy of diabetes mellitus. Gene Therapy 7: 181-182.*
Xu et al. (2003) Diabetes gene therapy: Potential and challenges. Current Gene Therapy 3(1): 65-82.*
Harrison's Principles of Internal Medicine, 12th ed., Eds. J.D. Wilson et al., McGraw-Hill, Inc., NY, 1991, vol. 1, p. 43.

Goodman and Gilman, The Pharmacological Basis of Therapeutics, 8th ed., Pergamon Press, 1990, pp. 1190-1191, 1281-1282, 1323-1324, 1342, 1509.
Anderson, WF, Nature, 392:25-30, 1998.
Dukes et al., Diabetes, 45(7):845-53, 1996.
Hughes et al., Proc. Nat'l. Acad. Sci., USA, 89:688-692, 1992.
Kaufman, J.E. et al., "Proinsulin Conversion in GH3 . . . ," Diabetes, 46:978-982, 1997.
Ledley, F.D., Pharmaceutical Research, 13:1595-1614, 1996.
Lipes, M.A. et al., "Insulin-Secreting Non-Islet . . . ," Proc. Nat'l. Acad. Sci., USA., 93:8595-8600, 1996.
Miller et al., FASEB J., 9:190-199.
Suzuki et al., Human Gene Therapy, 9:1223-1231.
Van Eyll et al., FEBs Letters, 348(1):7-13.
Zlokovic et al., Newrosurgery, 40(4):805-813.
Couzin, Islet transplants face test of time. Science 306 (5693):34-7 (2004).
Motoyoshi et al., Cellular characterization of pituitary adenoma cell line (AtT20 cell) transfected with insulin, glucose transporter type 2 (GLUT2) and glucokinase genes: insulin secretion in response to physiological concentrations of glucose. Diabetologia 41(12):1492-501 (1998).
The Diabetes Control and Complications Trial Research Group, The effect of intensive treatment of diabetes on the development and progression of long-term complications in insulin-dependent diabetes mellitus. New England J. Med. 329:977-986 (1993).
Tremblay et al., Pituitary-specific expression and glucocorticoid regulation of a proopiomelanocortin fusion gene in transgenic mice. Proc. Natl. Acad. Sci. U.S.A. 85(23):8890-4 (1988).
Zhang, Diabetes Care, Risk of developing retinopathy in Diabetes Control and Complications Trial type 1 diabetic patients with good or poor metabolic control. 24:1275-79 (2001).

* cited by examiner

*Primary Examiner*—Anne-Marie Falk
(74) *Attorney, Agent, or Firm*—Fish & Richardson P.C.

(57) ABSTRACT

The invention is directed to immunologically privileged cells, e.g., autologous, allogeneic, and xenogeneic intermediate lobe pituitary cells, for delivering polypeptides, e.g., insulin, to a subject, and to methods of using the same.

10 Claims, 7 Drawing Sheets

PANEL (A)

PANEL (B)

IMMUNOLOGICALLY PRIVILEGED CELLS AND USES THEREOF

This is a divisional application of U.S. patent application Ser. No. 09/127,296, filed Jul. 30, 1998, which is a continuation-in-part of U.S. Provisional application Ser. No. 60/054,730, filed Aug. 5, 1997, which is incorporated by reference.

GOVERNMENT RIGHT

This invention was made with government support under grant numbers DK 53281 and DK 53087 awarded by the National Institutes of Health. The government has certain rights in the invention.

BACKGROUND OF THE INVENTION

The invention relates to immuno privileged cells and the use thereof in tissue transplant and cell-based therapies.

Insulin dependent diabetes mellitus (IDDM) in humans and in non-obese diabetic (NOD) mice is an immune-mediated disorder in which mononuclear cells invade the pancreatic islets of Langerhans (insulitis) and effect the selective destruction of insulin-secreting pancreatic β cells (Eisenbarth G. S. (1983) *N. Engl. J. Med.* 308, 322–27). Since the introduction of insulin therapy in 1922, the majority of acute deaths due to insulin deficiency have been prevented. However, current insulin treatment regimens are still suboptimal for blood glucose control and patients with IDDM are at significant risk for the development of serious long-term complications such as blindness and kidney disease. Although progress is being made in the field of allogeneic islet transplantation as an alternative approach to the treatment of IDDM, the clinical applicability of this approach has been severely limited by the scarce supply of available islets and the rapid and aggressive recurrence of autoimmune disease in transplanted islet grafts, which occurs despite treatment with systemic immunotherapy (Tyden et al., NEJM, 1996).

Hepatocytes and the anterior pituitary tumor cell line, AtT20, have been studied as potential insulin producing cells. Proinsulin, when transfected into hepatocytes, which have only a constitutive pathway of protein secretion is processed to insulin extremely inefficiently (Valera, A., Fillat, C., Costa, C., Sabater, J., Visa, J., Paujol, A. & Bosch, F. (1994) *FASEB J.* 8, 440–447; Kolodka, T. M., Finegold M., Moss L, Woo S. L. C. (1995) *Proc. Natl. Acad. Sci. USA* 92 3293–3297). AtT20 cells have a regulated secretory pathway, with characteristic secretory granules containing the prohormone endopeptidases PC2 (Smeekens, S. P., Avruch, A. S., LaMendola, J., Chan, S. J. & Steiner, D. F. (1991) *Proc. Natl. Acad. Sci. USA* 88, 340–344), PC1/PC3 (Seidah, N. G., Marcinkiewicz, M. & Benjannet, S. (1991) *Mol. Endocrinol.* 5, 111–122), and carboxypeptidase H (Davidson, H. W. & Hutton, J. C. (1987) *Biochem. J.* 245, 575–582) that normally convert the prohormone proopiomelanocortin (POMC) to ACTH and other peptides. Proinsulin, when transfected into AtT20 cells, is processed to mature insulin, identical in structure to native (i.e., β-cell derived) insulin (Moore, H.-P., Walker, M. D., Lee, F., & Kelly R. B. (1983) *Cell* 35, 531–538; Ferber, S. Gross, D. J., Villa-Komaroff, L., Vollenweider, F., Meyer, K., Loeken, M., Kahn, C. R. & Halban, P. A. (1991) *Mol. Endo.* 5, 319–326). A major limitation of using transfected anterior pituitary cells for insulin gene delivery is that their major endogenous secretory product is ACTH, and, thus, implantation of these cells into diabetic recipients can result in a severe Cushings-like hypercortisolemic syndrome (Beltran-delRio, H., Schnedl, W. J., Ferber, S. & Newgard C. B. in *Pancreatic Islet Transplantation*, Vol 1, Lanza, R. P and Chick, W. L., Ed., R. G. Landes Company, Austin, pp 169–178, 1994). In addition, AtT20 cells, like many transformed β-cell lines, have an active constitutive pathway, with proinsulin comprising up to 25% of the secreted immunoreactive insulin (Gross, D. J., Halban, P. A., Kahn, C. P. Weir, G. C., Villa-Komaroff, L. (1989) *Proc. Natl. Acad. Sci. USA* 86, 4107–4111).

SUMMARY OF THE INVENTION

The inventor has discovered that immunologically privileged cells, e.g., intermediate lobe pituitary cells, are particularly suited for delivering polypeptides, e.g., insulin, to a subject. These cells are highly resistant to the autoimmune attack characteristic of IDDM.

Embodiments of the invention include implanting immunologically privileged cells (including, for example, intermediate lob pituitary cells and Sertoli cells) in order to deliver proteins which are not normally expressed in such cells to a subject. Such cells, even if non-autologous, do not trigger the normal immune response when introduced systemically. Therefore, they are resistant to damage or destruction in vivo. These cells are also resistant to autoimmune attack. This makes them well-suited for delivering insulin for treatment of IDDM because they will not be destroyed following introduction by the autoimmune response which normally depletes the insulin-producing β cells in individuals with IDDM.

In embodiments of the invention, the immunologically privileged cells are transfected with a heterologous nucleic acid sequenc, e.g., a protein encoding sequence, prior to systemic introduction. They can be transfected with a control region which is active in the cell. Such control regions include intermediate lobe pituitary cell specific promoters, enhancers or other control elements; a POMC promoter, or a CMV promoter. In a preferred embodiment, the cells are animal-derived intermediate lobe pituitary cells and the control region is from the same species as the cell.

In the embodiments preferred for human therapy, a heterologous nucleic acid sequence encoding a human therapeutic protein, for example, insulin, is transfected into an animal-derived immunologically privileged cell, and the cell is implanted systemically in a subject. If the protein expressed is insulin, its secretion from the cells must be controlled in a glucose stimulated manner in order to properly regulate insulin levels in vivo. This is accomplished by having the cells transfected to also express proteins necessary to exercise such control. These additional proteins can include one or more of and preferably all of: glucose phosphorylating protein, e.g., glucokinase with a high Km for glucose, and preferably, the β-cell isoform of glucokinase; a GLUT family member, e.g., GLUT-1, GLUT-3 or GLUT-5, and preferably GLUT-2 or another high Km glucose transporter; an ion channel which mediates glucose-stimulated insulin release, e.g., a K+/ATP ion channel, preferably, the sulfonylurea receptor/Kir 6.2 channel; and glucagon-like peptide-1 (GLP-1).

Examples of other proteins which can be expressed in immunologically privileged cells include growth hormone, a hematopoietic hormone or growth factor, or a cytokine or lymphokine. The protein expressed would preferably be native to humans where intended for human treatment, but could also be native to animals if such protein was suitable for human treatment of the cells where intended for veterinary use.

The nucleotide sequences encoding any of the proteins to be expressed, or any of the control regions, can be inserted into the cell by standard transfection methods, e.g., adenoviral or retroviral gene delivery. These nucleotide sequences are preferably integrated into the chromosome of the cells.

A number of variations of the invention described above are feasible and readily apparent to one skilled in the art. For example, the cells can be human or animal-derived, and include cells which are bovine, porcine, rodent (e.g., rat or mouse), or nonhuman primate derived. The protein expressed can be from the same or a different species from the cells, and can be autologous or non-autologous. The immunologically privileged cells can be cultured cells or cells derived from a transgenic animal. The cells can also be autologous cells which are transfected ex vivo with nucleotides coding for the protein(s) one wishes to express, and then introduced into the subject. The cells can also be allogeneic, that is, a human cell from another human being not the subject, or xenogeneic, from another species. One preferred intermediate lobe pituitary cell is a fetal or post natal cell. The cells may also be encapsulated in a non-antigenic coating, e.g., a hydrogel, an alginate compound, or a polymer (preferably a polymer which forms a semipermeable layer).

As noted above, the immunologically privileged cells which express proteins can be introduced into humans or into non-human animals for veterinary uses. The therapy can be used in conjunction with immunosuppressants, for example, cyclosporine. Further, more than one therapeutic or beneficial protein can be expressed in a particular cell, if desired.

In another embodiment, the invention includes using gene therapy techniques to transfect, in vivo, intermediate lobe pituitary cells with nucleotides which promote the expression of a protein. The nucleic acid can, by way of example, when integrated into the chromosome, stimulate the expression of an endogenous sequence. The nucleic acid can also encode a therapeutic or beneficial protein or proteins. Such proteins include growth hormone, a hematopoietic hormone or growth factor, or a cytokine or lymphokine, or insulin. Another embodiment of the invention includes using gene therapy techniques to transfect, in vivo, immunologically privileged cells (including intermediate lobe pituitary cells) with nucleotides which promote the expression of insulin and other proteins, in order to express insulin in a glucose stimulated insulin secreting manner. In yet another embodiment, the invention includes using gene therapy techniques to transfect, in vivo, other cell types to express insulin in a glucose stimulated insulin secreting manner.

For any of these gene therapy embodiments, the transfection of the cells can be effected by conventional methods, including adenoviral or retroviral gene delivery. The nucleotide transfected encodes a protein not normally expressed by the target cell and operatively linked to a heterologous control region which supports expression of the nucleotide in the target cells. These techniques can be used in humans or non-human animals. Preferably, the subject is immunosuppressed by providing an immunosuppressant, e.g., cyclosporine before the transfection.

The cell should also be transfected with a promoter, enhancer, or other control element, which is preferably active in the cells and included as part of the transfected nucleotide sequence, including POMC and a CMV promoter. For cells which are transfected to express insulin, they are preferably also transfected with oen or moare and preferrably all or: a glucose phosphorylating protein, e.g., glucokinase with a high Km for glucose and preferably, the β-cell isoform of glucokinase; a GLUT family member, e.g., GLUT-1, GLUT-3 or GLUT-5, and preferably GLUT-2 or another high Km glucose transporter; an ion channel which mediates glucose-stimulated insulin release, e.g., a K+/ATP ion channel, preferably, the sulfonylurea receptor/Kir 6.2 channel; and glucagon-like peptide-1 (GLP-1). In such a case, the cells are also transfected with control regions for expression of such proteins.

As another variation, in the case where insulin is expressed (whether the expressing cells are modified ex vivo or transfected in vivo), one can evaluate a parameter relating to glucose metabolism in connection with controlling insulin secretion. The parameter can include: the amount, distribution or structure of intracellular or extracellular insulin; glucose phosphorylating activity; or the amount, distribution, or structure of insulin encoding RNA; glucose utilization; glucose uptake; or insulin secretion The invention also includes immunologically privileged cells, or purified preparations thereof, discussed herein. As discussed herein, the cells have been engineered to express a protein they do not normally express. The cell can be an intermediate lobe pituitary cell, which expresses a human protein it does not otherwise express, e.g., human insulin. The cell can include one or more of and preferably all of:

an insulin-encoding nucleic acid operatively linked to a control region other than the insulin control region, e.g., a control region which allows expression in intermediate lobe pituitary cells, e.g., a POMC promoter;

a nucleic acid which encodes GLUT-2 operatively linked to a control region other than the GLUT-2 control region, e.g., a control region which allows expression in intermediate lobe pituitary cells, e.g., a POMC promoter;

a nucleic acid which encodes a glucokinase, preferably the β cell isoform of glucokinase, operatively linked to a control region other than the glucokinase control region, e.g., a control region which allows expression in intermediate lobe pituitary cells, e.g., a POMC promoter; and a nucleic acid which encodes GLUT-2 operatively linked to a control region other than a GLUT-2 control region, e.g., a control region which allows expression in intermediate lobe pituitary cells, e.g., a POMC promoter;

a nucleic acid which encodes a glucokinase, preferably the β cell isoform of glucokinase, operatively linked to a control region other than a glucokinase control region, e.g., a control region which allows expression in intermediate lobe pituitary cells, e.g., a POMC promoter;

a nucleic acid which encodes an ion channel which mediates the expression of insulin, e.g., $K^+_{ATP}$ channel, operatively linked to a control region other than an ion channel control region, e.g., a control region which allows expression in intermediate lobe pituitary cells, a POMC promoter; and a nucleic acid which encodes GLP-1, operatively linked to a control region other than a GLP-1 control region, e.g., a control region which allows expression in intermediate lobe pituitary cells, a POMC promoter.

The intermediate lobe cell can be a non-human or human cell.

In another aspect, the invention features, a cell described herein, encapsulated with an non-antigenic coating.

The coating can include a hydrogel, e.g., an alginate compound. It can include a polymer, e.g., a polymer which forms a semipermeable layer.

The invention also includes a transgenic animal, preferably a non-human animal, e.g., a transgenic swine or a transgenic mouse, having a peptide not normally expressed in intermediate lobe pituitary cells, e.g., insulin. The peptide can be expressed under the control of a promoter which allows expression in pituitary cells, or under the control of a promoter which is pituitary specific, e.g., a POMC promoter.

If the protein expressed is insulin, its secretion from cells must be controlled in a glucose stimulated manner in order to properly regulate insulin levels in vivo. This is accomplished by including transgenes which express proteins necessary to exercise such control. These additional proteins can include one or more of and preferably all of: glucose phosphorylating protein, e.g., glucokinase with a high Km for glucose, and preferably, the β-cell isoform of glucokinase; a GLUT family member, e.g., GLUT-1, GLUT-3 or GLUT-5, and preferably GLUT-2 or another high Km glucose transporter; an ion channel which mediates glucose-stimulated insulin release, e.g., a K+/ATP ion channel, preferably, the sulfonylurea receptor/Kir 6.2 channel; and GLP-1.

Examples of other proteins which can be expressed in immunologically privileged cells include growth hormone, a hematopoietic hormone or growth factor, or a cytokine or lymphokine. The protein expressed would preferably be native to humans where intended for human treatment, but could also be native to animals if such protein was suitable for human treatment of the cells where intended for veterinary use.

Transgenic animals can be used to provide genetically engineered intermediate lobe cells described herein and the invention includes such animals.

The invention also includes a subject, e.g., a non-human animal or a human, which has an intermediate lobe pituitary cell which express a peptide not normally expressed in intermediate lobe pituitary cells. E.g., the subject has disposed within its body an intermediate lobe pituitary cell described herein.

If the protein expressed is insulin, its secretion from the cells must be controlled in a glucose stimulated manner in order to properly regulate insulin levels in vivo. This is accomplished by having the cells transfected to also express proteins necessary to exercise such control. These additional proteins can include one or more of and preferably all of: glucose phosphorylating protein, e.g., glucokinase with a high Km for glucose, and preferably, the β-cell isoform of glucokinase; a GLUT family member, e.g., GLUT-1, GLUT-3 or GLUT-5, and preferably GLUT-2 or another high Km glucose transporter; an ion channel which mediates glucose-stimulated insulin release, e.g., a K+/ATP ion channel, preferably, the sulfonylurea receptor/Kir 6.2 channel; and GLP-1.

Examples of other proteins which can be expressed in immunologically privileged cells include growth hormone, a hematopoietic hormone or growth factor, or a cytokine or lymphokine. The protein expressed would preferably be native to humans where intended for human treatment, but could also be native to animals if such protein was suitable for human treatment of the cells where intended for veterinary use.

In preferred embodiments, the subject is a dog, goat, sheep, cow, pig, a rodent, e.g., a mouse or rat, a primate, or a human.

As used herein, a nucleic acid which promotes the expression of a protein is a nucleic acid which when introduced into the cell increases the level of the protein. Thus, the nucleic acid can, e.g., encode the protein, or can be a control region which can, when introduced, e.g., integrated, modulates the expression of the gene product.

Immunologically privileged cells resist immune rejection when grafted into conventional (non privileged) sites (e.g., renal capsule). Such known tissues include the brain, testes (Sertoli cells), eye, placenta, cornea, and as shown herein, the IL (but not the AL) of the pituitary. Preferred immunologically privileged cells exhibit one or more of: reduced or absent expression of class I and II MHC molecules, secretion of immunosuppressive cytokines, intratissue structural barriers, and constitutive expression of Fas ligand. Privileged tissues are distinct from immune privileged sites. [J W Streilein *Science* 270 1158–1159 (1995)]. Immune-privileged sites are regions of the body where grafts of foreign tissue survive for extended periods (even indefinitely), compared to conventional (non privileged) sites. Immune privileged sites include the eye and the brain, which are located behind blood-tissue barriers. Because the pituitary, like the eye, lacks lymphatic drainage [A. Hoek, W Allaerts, P J M Leenen, J Schoemaker & H A Drexhage *Eur J Endo* 136 8–24 (1997)] it is possible that antigenic material contained inside the pituitary could remain invisible to the immune system. This anatomic feature of the pituitary may protect it from immune attack.

The terms "peptides", "proteins", and "polypeptides" are used interchangeably herein.

Insulin dependent diabetes mellitus (IDDM) is caused by autoimmune destruction of insulin producing β-cells. Islet transplantation has been extensively investigated as a strategy for curing IDDM, but suffers from the difficulties associated with procuring sufficient tissue and from recurrent autoimmunity in the transplanted islet grafts. The present invention is based in part on the inventor's recognition that the islet autoimmunity can be circumvented with the use of immunoprivileged intermediate lobe pituitary cells engineered to secrete insulin. Such cells can be grown in quantity in vitro and can be used to replace daily insulin injections as therapy for Type I diabetes.

Although insulin has been implicated as a major autoantigen in IDDM (Wegmann, D. R., Norbury-Glaser, M. & Daniel, D. (1994) *Eur. J. Immunol.* 24, 1853–1867; Eisenbarth, G. S. (1994) *Diabetes Care* 17(6), 605–607.), pathologic lesions did not develop in the insulin-secreting pituitaries of the transgenic NOD mice having a transgene which expresses insulin in the intermediate lobe pituitary (see below). Likewise, transplantation of the transgenic pituitaries under the kidney capsules of diabetic (nontransgenic) NOD recipients did not, in contrast to transplanted islets, provoke autoimmune infiltration or destruction of the grafts (see below). The ability of the insulin-producing intermediate lobe pituitaries to elude immune system recognition and attack, is highly advantageous for transplantation purposes.

Intermediate lobe pituitary (IL) cells have several advantages compared to the previously described ACTH-producing anterior pituitary cells (AT20 cells) for targeted insulin gene delivery. Firstly, due to tissue specific differences in prohormone processing, ACTH is further processed in intermediate lobe cells to α-MSH (ACTH 1–13) and CLIP [ACTH 18–39] neither of which are known to have adverse metabolic effects. Secondly, despite relatively small size (<25% of the mass of the anterior pituitary), the engineered intermediate lobe cells expressed high levels of insulin, sufficient to cure diabetes in NOD mice. Thirdly, the intermediate lobe pituitary grafts had markedly better viability than anterior pituitary lobe grafts: when transplanted long-term (>100 days) under the kidney capsule the anterior pituitary cells, with the exception of the lactotrophs, became atrophied whereas the intermediate pituitary grafts remained viable and continued to produce abundant amounts of hormones, similar to previous studies. These findings, reminiscent of changes following pituitary stalk transection are due to the differential regulation of these two cell types: whereas secretion from most anterior lobe cells is dependent upon stimulation by trophic hypothalamic hormones, secretion from intermediate lobe pituitary cells is predominantly under tonic inhibitors control by dopamine. Finally, it is shown herein that in contrast to IL lobe tissues anterior lobe pituitary tissues, when transplanted under the kidney capsule, are subject to aggressive autoimmune attack and destruction in NOD mice.

Thus embodiments of the invention address a major barrier to the transplantation of islets in individuals with IDDM—the development of rapid and aggressive recurrent autoimmune disease in transplanted islet grafts. Although treatment with sustained immunosuppressive drugs can prevent islet allorejection, it is less effective in preventing the autoimmune destruction of insulin-producing β cells in islet grafts. Intermediate lobe pituitary cells genetically engineered to produce insulin (ILins) are capable of treating diabetes when transplanted into a subject, but are not subject to this immune system attack.

This important feature has been demonstrated in a variety of experiments, summarized here:
1. When implanted under the kidney capsule of spontaneously diabetic NOD mice, the insulin-producing IL pituitary cells did not become infiltrated by the cells of the immune system while islets implanted under the opposite kidney capsule were rapidly targeted and destroyed;
2. Insulin-producing IL tissues cured diabetes when transplanted into spontaneously diabetic NOD mice. Examination of the IL grafts at the end of transplantation period showed healthy grafts that were devoid of evidence of immune system attack and that contained abundant amounts of insulin. In contrast, diabetic mice similarly transplanted with insulin-producing islet grafts developed recurrence of their diabetic symptoms with the islet grafts becoming severely infiltrated by cells of the immune with complete destruction of the insulin-producing β cells;
3. When islet and insulin-producing IL cells were mixed together and co-transplanted into diabetic NOD mice, severe lymphocytic infiltration developed over the entire graft, including areas containing IL cells. Although the insulin-producing islet β-cells were completely destroyed, the insulin-positive IL cells remained intact. Indeed, all of the insulin-positive cells that remained in the grafts at the end of the transplantation period colocalized with POMC-peptides and were thus pituitary-derived. Thus, even when placed in direct contact with diabetogenic infiltrates, the ILins cells were resistant to autoimmune-mediated cell destruction;
4. In other experiments, streptozotocin-induced diabetic scid (severe combined immunodeficient) NOD mice were transplanted with similar amounts of insulin-producing tissues (110 islets and 2 ILins pituitaries) under the opposite kidney capsules. When their immune system was reconstituted with $20 \times 10^6$ cells of a highly pathogenic insulin-specific T cell clone (PD-12-4.4), they developed recurrence of their diabetic symptoms. As expected, their islet grafts became severely infiltrated with loss of the insulin-producing β cells. In contrast, examination of the insulin-producing IL grafts transplanted under the contralateral kidney capsule of these mice showed no evidence of infiltration by these clones, even though they are specifically reactive to insulin. Indeed, the ILins grafts in scidNOD mice that received the insulin-specific "killer" T cells contained abundant insulin-staining cells, similar in appearance to ILins grafts of control scidNOD mice that only received saline.

These results demonstrate that the IL pituitary cells can evade recognition and destruction by autoaggressive cells of the immune system in IDDM. The protection of IL from autoimmune recognition is a unique feature that is clearly advantageous, especially for transplantation purposes. The inventor has discovered that similar to other immunologically privileged sites (eye, testes, brain), cells of the IL pituitary constitutively express transcripts for Fas ligand. The expression of Fas ligand has been shown to help maintain the integrity of immune privileged sites. (S. W. Streilein, *Science* 270:1158–1159 (1995)). See FIG. 4C. In addition, like other immunoprivileged tissues, IL cells have low or absent levels of class I and class II MHC molecules.

The ability of these cells to resist immune attack and injury applies not only to recurrent autoimmunity but it also applies to allograft rejection. See FIG. 4B. Whereas islet allografts (islet) (BALB/c→C3H) became severely rejected and necrotic with few insulin-positive cells remaining, intermediate lobe allografts (IL pituitary) transplanted under the opposite kidney capsules were well vascularized and showed abundant amounts of healthy-appearing cells which stained intensely with POMC peptide antisera and had minimal evidence of infiltration.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

DETAILED DESCRIPTION OF CERTAIN EMBODIMENTS OF THE INVENTION

The drawings will first be briefly described.

Drawings:

FIG. 1 is a depiction of the major cellular events in glucose-induced insulin secretion in pancreatic β cells.

FIG. 2 is a schematic diagram depicting the construction of the rat proopiomelanocortin (POMC)/mouse preproinsulin II (POMC-Ins) fusion transgene. P=prepeptide coding region; B=B-chain coding region; C=C-peptide coding region; A=A-chain coding region; exons 1–3 (E1–3) are as indicated. Segments of Primer 3 (SEQ ID NO: 4), PPI-2 (SEQ ID NO: 5), and Primer 1 (SEQ ID NO: 6) are also shown.

FIG. 3 is a graph depicting the effect of transplanting transgenic insulin-producing intermediate lobe tissues into spontaneously diabetic NOD mice. (A) Percent weight change and (B) blood glucose levels in diabetic NOD mice following transplantation with transgenic intermediate lobe pituitaries (circles) or transplanted with nontransgenic control intermediate lobe pituitaries (triangles) calculated from day 0. Each point was the mean percent weight change, or the mean blood glucose level, ±SE.

FIG. 4A is a photographic representation of histological analysis of serial sections of islet ("Islets") and insulin-producing IL pituitary ("IL Pituitary") grafts in diabetic NODscid recipients that received 20×10$^6$ cells of the insulin-specific T cells clone, PD12-4.4 (left panels, "Insulin-Specific T cell Clone", or control saline (right panels, "Saline"). Twenty days after receiving these T cells clones, there was selective destruction of insulin-producing islet β cells (Ins, middle panel), with only non-insulin positive cells remaining (Glucagon, lower panel). In contrast, the insulin producing IL grafts were not destroyed by the insulin-specific clones and these tissues expressed abundant amounts of insulin staining (Ins, middle panel) which co-localized with ACTH (lower panel) staining, similar in appearance to the IL grafts of mice that received control saline.

FIG. 4B depicts islet and IL pituitary allografts transplanted from C3H donor mice into the renal capsule of BALB/c recipients. Top panels: Islet (left) and IL pituitary (right) allografts photographed from a Leica M8 Wild stereo-dissecting microscope. Bottom panels: immunhistology of islet allografts stained with insulin ("Ins") antisera and IL pituitary allografts stained with ACTH ("ACTH") antisera.

Figure 6:
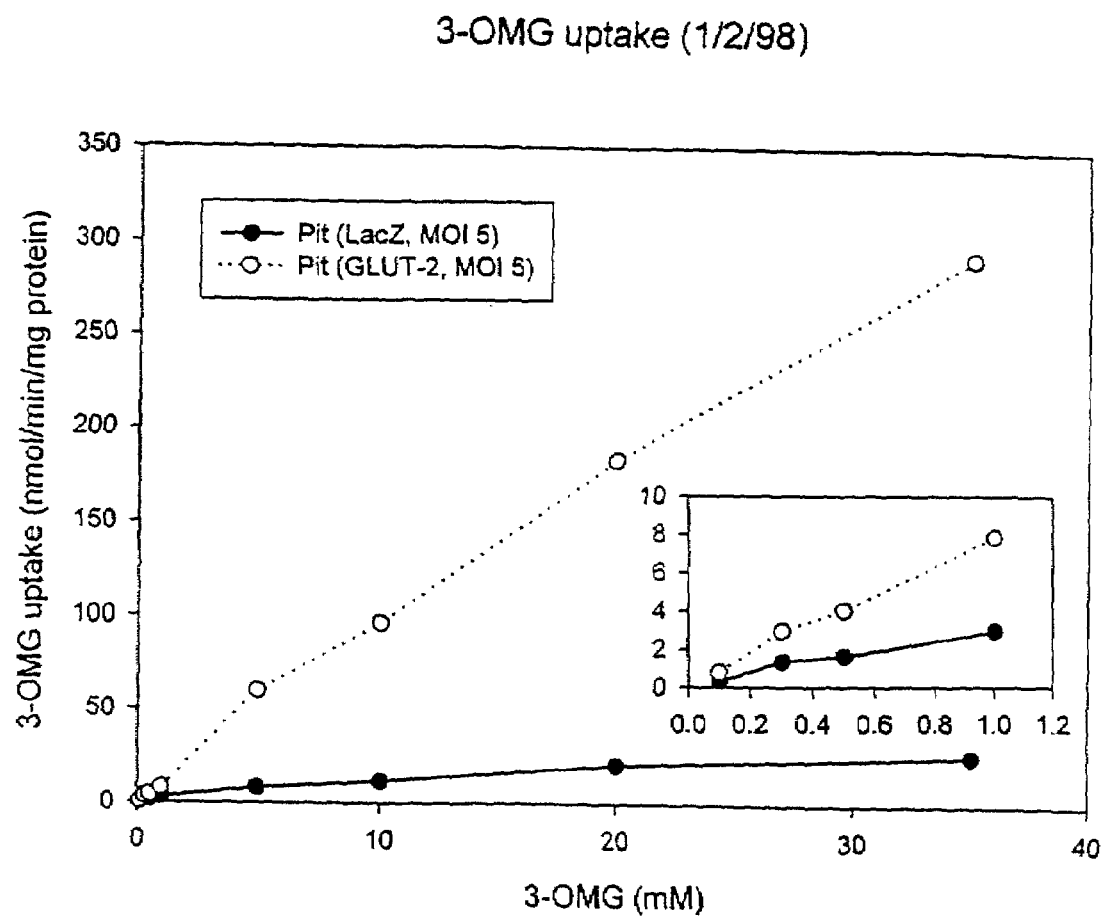

FIG. 6 is a depiction of glucose uptake in GLUT-2 transfected insulin-producing IL cells, as assayed by 3-O-methylglucose uptake under zero-trans conditions. This figure shows that glucose transport in the LacZ control transfected ILins cells was minimal, since they only express GLUT-1, whereas in the ILins/GLUT-2 expressing transgenic cells, glucose transport kinetics were similar to islets, which have a $K_m$ of 18 mM for glucose and a $V_{max}$ of 24 mmol/min per liter of cell space.

Figure 7:
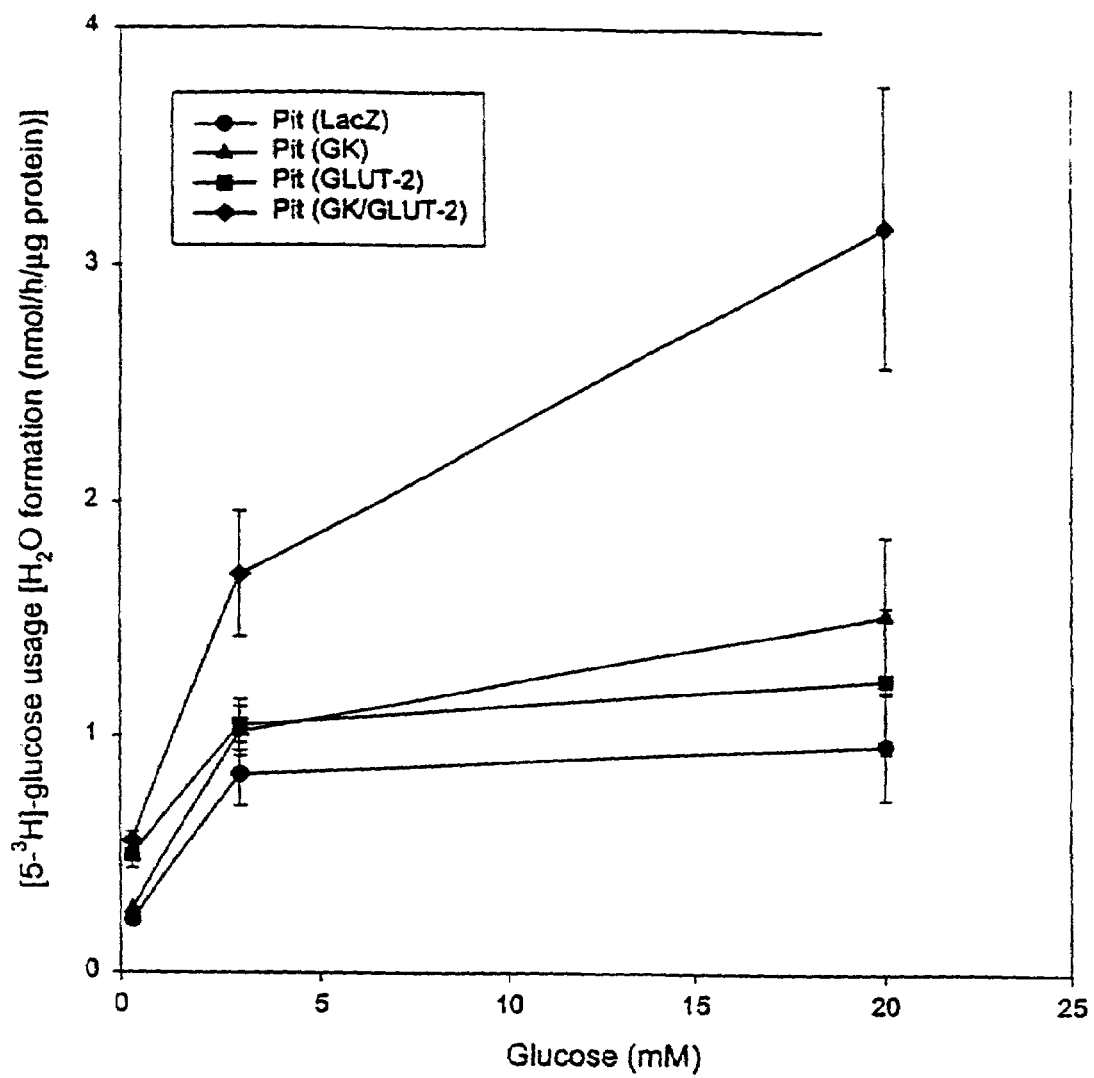

FIG. 7 is a graph of glucose usage in intermediate lobe pituitary cells transduced with adenoviruses containing control LacZ, the islet isoform of glucokinase (GK) and/or the GLUT-2 gene. Each point represents the mean±S.E. for three separate experiments.

INTERMEDIATE LOBE PITUITARY CELLS AS VEHICLES FOR INSULIN REPLACEMENT THERAPY

Intermediate lobe pituitary cells which have been genetically engineered to express insulin are not subject to the autoimmune attack characteristic of IDDM and are resistant to allograft rejection. As is discussed herein, insulin expression is normally absent in intermediate lobe pituitary cells. In order to provide insulin expression, an insulin gene was coupled to a promoter which is active in intermediate lobe pituitary cells. As is discussed herein, the cells can also be engineered to express proteins which confer glucose-sensitive expression on the cells. E.g., the cells can be engineered to express one or more of a glucose transport protein, glucokinase, an L-type Ca2+ channel, or a $K^+_{ATP}$ channel, or GLP-1. The genes should be expressed at a level sufficient to confer glucose-regulated regulated insulin secretion. The engineered cells can be used to supply insulin to a subject in need of insulin, e.g., a subject suffering from IDDM.

The disclosure set out herein describes how murine intermediate lobe pituitary cells can be analyzed to determine what modifications, in terms of genetically engineering the cells, are needed to allow the cells to express insulin and to release the insulin in a glucose-sensitive fashion. These methods can be applied to intermediate lobe pituitary cells from other species to determine what steps need to be taken to confer on the cells the ability to express insulin and the ability to release insulin in a glucose-sensitive fashion. The first step will generally be to determine if the intermediate lobe pituitary cell expresses insulin, and elements of the glucose sensing machinery, e.g., glucose transport proteins, glucokinase, and a $K^+_{ATP}$.channel. If insulin is not expressed at a level which will provide normal glucose homeostasis, then the cells are genetically engineered to express insulin at such levels. This can be accomplished by providing an insulin encoding nucleic acid operatively linked to a heterologous promoter which supports expression in intermediate lobe pituitary cells. If proteins which support glucose sensing, e.g., glucose transport proteins and glucokinase, are not expressed at levels sufficient to confer glucose mediated release of insulin, then the cells are engineered to express these proteins at levels which allow glucose sensing. Guided by the disclosure provided herein, one skilled in the art will be able to determine the levels of expression of the relevant genes in a subject cell, engineer the cells to express those genes which are needed for insulin expression and glucose-sensitive release, and test the subject engineered cells for the desired properties.

Although much of the disclosure herein is directed to the use of intermediate lobe cells to deliver insulin, one skilled in the art can, guided by the specification and using analogous methods, engineer intermediate lobe cells (or other immunologically privileged cells) to express and deliver other proteins. Such cells can be used to provide other desirable proteins to a subject. The type of engineering that will be required in order to produce a cell that secretes a desired polypeptide will depend on the polypeptide. One or more of these genes will generally be a recombinant gene. In many cases the cell will be genetically engineered so as to include a nucleic acid which encodes the desired peptide operatively linked to a heterologous control region.

Recombinant genes should be placed under the control of a control region which directs sufficient expression of the gene in the intermediate lobe pituitary cells. Tissue specific promoters can be used. Tissue specific promoters, that is promoters which express in the immunologically privileged cells but not in some or all other cell types, may be more desirable where a transgenic animal is used to supply genetically engineered tissue, as the genes will not be expressed in all cells of the transgenic animal. The POMC promoter is particularly suited for use with intermediate lobe pituitary cells. Constitutive promoters can be used. Constitutive promoters include viral promoters, for example, cytomegalovirus promoters, and SV-40 early gene promoters.

The use of Intermediate Lobe Pituitary Cells in β Cell Replacement

Glucose Sensing

The initial protein product of the insulin gene is preproinsulin. This precursor molecule includes an N-terminal signal or presequence which directs the gene product to the rough endoplasmic reticulum. Preproinsulin is processed on the rough endoplasmic reticulum into proinsulin, which lacks the signal peptide. Proinsulin includes sequence which corresponds to the A chain of insulin, sequence which corresponds to the C-peptide, and sequence which corresponds to the B chain of insulin. Proinsulin is transported to the golgi apparatus and then to the secretory granules. The C-peptide is enzymatically removed from proinsulin in the secretory granules. The secretory granules bud, migrate to the surface of the cell, and fuse with the plasma membrane to release mature hormone. The mature hormone consists of two polypeptide chains, A and B.

Although insulin secretion from islet β cells is influenced by a wide variety of factors, the most important is glucose. In contrast to the mode of action of hormones such as insulin that bind to membrane-bound receptors, glucose sensing is mediated by its entry into β cells and through the generation of metabolic signals. Glucose-induced insulin secretion requires the metabolism of glucose; nonmetabolizable analogs of glucose such as 2-deoxyglucose are ineffective at promoting insulin release. Insulin secretion and the rate of glucose metabolism in β cells increase in parallel to elevations in the extracellular glucose concentration over the range 5–30 mM.

Figure 1:
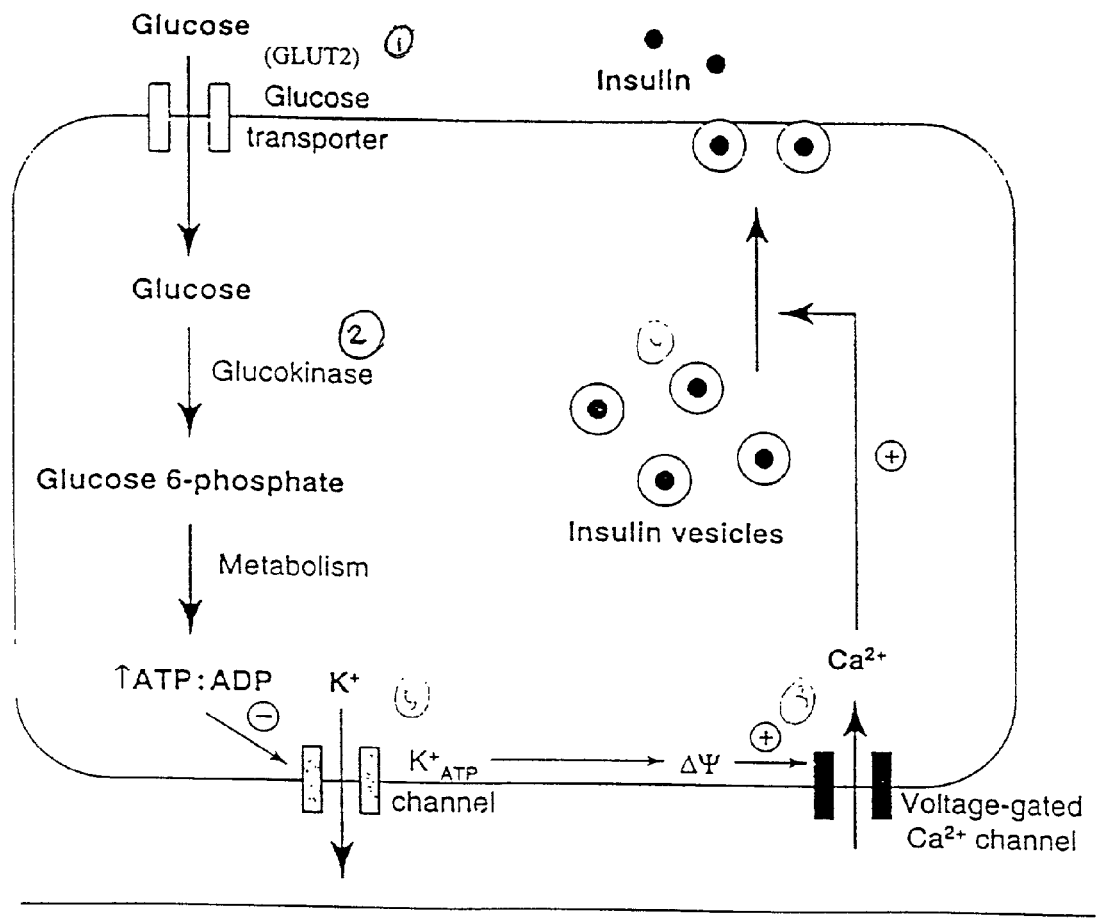

The exact sequence of biochemical events involved in glucose-stimulated insulin secretion has not yet been defined, but it appears that the metabolism of glucose in the β cell generates the conversion of ADP to ATP, which leads to the closure of the ATP-sensitive $K^+$ ($K_{ATP}$) channels. The resulting plasma membrane depolarization opens voltage-gated $Ca^{2+}$ channels and induces an influx of $Ca^{2+}$, which triggers $Ca^{2+}$-dependent exocytosis of insulin secretory granules. The major cellular events in glucose-induced insulin secretions in pancreatic β cells is depicted in FIG. 1. Glucose is transported into the cell by the glucose transporter GLUT2. It is then phosphorylated by glucokinase. Further glucose metabolism generates signals that inhibit the ATP-sensitive $K^+$ channels, resulting in membrane depolarization. This activates the voltage-gated $Ca^{2+}$ channels and increases intracellular $Ca^{2+}$ levels. $Ca^{2+}$ in turn triggers the fusion of prestored insulin in secretory granules with the plasma membrane.

The proteins that control the metabolic flux of glucose in β-cells function as "glucose sensors" and couple changes in the extracellular glucose concentrations to changes in insulin secretion. Two specialized proteins are of particular importance in glucose sensing: the facilitated glucose transporter isotype, GLUT-2, and the glucose phosphorylating enzyme, glucokinase. These and other glucose sensitive molecules, including GLP-1, are discussed in greater detail below.

Glucose Transport Proteins

The ability of a cell to respond to physiological concentrations of glucose with an appropriate level of insulin release can be increased by expression in the cell of a glucose transport protein.

In most mammalian cells, glucose is transported across the plasma membrane by members of a family of facilitated glucose transport proteins, which are identified by the acronym GLUT. GLUT 1–5 have been characterized. These GLUT transporters have distinct kinetic properties and tissue distribution. GLUT2 differs from other members of the GLUT family in that it has a distinctly higher Km and Vmax for glucose. As such, GLUT2 is the preferred glucose transporter for genetically engineering cells for glucose sensitivity. The sequence of human GLUT2 is described in Takeda et al., *Diabetes*, 1993, 42(5):773–7, hereby incorporated by reference.

Stable transfection of GLUT-2, the primary glucose transporter in the rodent βcell, into AtT20-ins cells results in glucose- stimulated insulin secretion, increased insulin content and glucose potentiation of non-glucose secretagogues (Hughes, S. D., Johnson, J. H., Quaade, C. & Newgard, C. J.: (1992) *Proc. Natl. Acad. Sci. USA* 89:688–692.). AtT-20ins cells transfected with GLUT-1 do not respond to glucose (Hughes, S. D., Quaade, C., Johnson, J. G., Ferber S. & Newgard, C. B.: (1993) *J. Biol. Chem.* 268(20): 15205–12.). When GLUT-2 is transfected into insulin-secreting cell lines, there is a four fold increase in glucokinase activity (Ferber, S., BeltrandelRio, H., Johnson, J. H., Noel, R. J., Cassidy, L. E., Clark, S., Becker, T. C., Hughes, S. D. & Newgard, C. B.: (1994) *J. Bio. Chem.* 269: 11523–11529). Although expression of GLUT-2 appears to be a necessary component in β cell sensing, it is not rate limiting since glucose-transport capacity appears to far exceed the rate of glucose metabolism in islets (Trus, M. D., Zawalich, W. S., Burch, P. T., Berner, D. K., Weill, V. A. & Matschinsky, F. M.: (1981) *Diabetes* 30:911–922).

Thus, a cell of the invention, e.g., an intermediate lobe pituitary cell, can include an engineered nucleic acid which promotes the expression of, e.g., encodes, a protein which promotes the transport of glucose across the plasma membrane (a glucose transport protein). The protein can be, e.g., a GLUT family member, e.g., GLUT-1, GLUT-2, GLUT-3, or GLUT-5. In particularly preferred embodiments, the nucleic acid promoter the expression of, e.g., encodes, GLUT-2, or another high Km glucose transporter.

Glucokinase

The ability of a cell to respond to physiological concentrations of glucose with an appropriate level of insulin release can be increased by expression in the cell of a protein which phosphorylates glucose.

Glucokinase appears to be the rate-limiting step in islet β cell glucose metabolism and may represent the main glucose sensor in the β cell. The key observations linking glucokinase activity and glucose-stimulated insulin release are the curve describing the glucose concentration dependence of glucose metabolism in islets is superimposable on that describing the glucose concentration dependence of glucokinase activity in islet cell extracts (Malaisse, W. J., Sener, A., Herchuelz, A. & Hutton, J. C.: (1979) *Metabolism* 28: 373–386; Meglasson, M. D. & Matschinsky, F. M.: (1986) *Diabetes Metab. Rev.* 2:163–214) and the demonstration that inhibitors of glucokinase activity block β-cell glycolysis and glucose-stimulated insulin release (Meglasson et al., 1986; Coore, H. G., Randle, P. J.: (1964) *Biochem J*91: 56–59). The sequence of human glucokinase can be found in Tanizawa Y et al. (*Mol. Endocrinol.* 1992 6(7):1070–81). Glucokinase is the high Km, high Vmax, member of the hexokinase family.

Glucokinase has a $K_m$ for glucose of approximately 8 mM, a feature which allows for large alterations in enzyme activity in response to modest increments in glucose concentration over the physiological range (4–9 mM). The activity of the low $K_m$ glucose phosphorylating enzyme, hexokinase ($K_m$=50 μM) actually exceeds glucokinase activity in normal islet extracts. Yet islets metabolize glucose inefficiently at submillimolar concentrations and exhibit no insulin secretory response to low concentrations of the sugar. The most logical explanation for these observations is that hexokinase is kept in an inhibited state in intact islet β cells, possibly by its allosteric effector glucose-6-phosphate, this preventing metabolism-induced secretion at subphysiological glucose concentrations. The glucokinase:hexokinase ratio may play an important role in dictating the dose threshold for glucose-stimulated insulin secretion.

Consistent with an important role for glucokinase, mutations in this gene are associated with β-cell dysfunction in a subtype of non-insulin-dependent diabetes mellitus known as maturity-onset diabetes of the young (MODY). In addition, mice lacking a functional glucokinase allele develop mild diabetes, comparable to MODY patients who are universally heterozygous for glucokinase mutations, and mice completely deficient in glucokinase activity are severely diabetic.

The glucokinase protein expressed in islets and pituitary cells is identical to that found in the liver except for the 15 $NH_2$-terminal amino acids. However, because of the preferential use in anterior pituitary cells of alternate RNA splice acceptor sites that disrupt the reading frame, glucokinase activity is absent. Thus, to genetically engineer glucokinase activity in cDNA's encoding functional islet glucokinase isoforms should be used.

Thus, a cell of the invention, e.g., an intermediate lobe pituitary cell, can include an engineered nucleic acid which promotes the expression of, e.g., encodes, a protein which phosphorylates glucose (a glucose phosphorylating protein), e.g., a glucokinase, preferably the β cell isoform of glucokinase. In preferred embodiments the glucokinase is a high Km glucokinase Glucagon-like Peptide-1 Receptor (GLP-1R).

The ability of a cell to respond to physiological concentrations of glucose with an appropriate level of insulin release can be increased by expression in the cell of a receptor for a hormone which potentiates insulin release.

Glucose-induced insulin secretion can also be modulated by a number of hormones and neurotransmitters. One hormone in particular, GLP-1, potentiates the effect of glucose on insulin secretion and has thus been called a glucoincretin. GLP-1 is produced mainly by the gut in response to food intake (especially carbohydrates) and exerts diverse insulinotropic actions on cells that include stimulation of cAMP production and insulin biosynthesis and secretion. GLP-1 is part of the preproglucagon molecule and is proteolytically processed in intestinal L cells to GLP-1-(1–37) and GLP-1(7–36)amide or GLP-1-(7–37). Only the truncated forms of GLP-1 are biologically active; GLP-1 (7–36) amide is the naturally occurring form in humans. These short peptides, the most potent gluco-incretins so far described, are active at concentrations as low as 1–10 pM. The action of GLP-1 is receptor-mediated; the β-cell GLP-1 receptor has been cloned and shown to bind GLP-1 (but not glucagon or other peptides) with high affinity (Thorens, B.: (1992) Proc. Natl. Acad. Sci. USA 89:8641–8645).

All insulinotropic actions of GLP-1 require the presence of glucose at or above the normal physiological concentration of about 5 mM, suggesting that GLP-1 acts as a potentiator of the β cell glucose signaling system. GLP-1 has been shown to confer glucose sensitivity to glucose-resistant β cells by interacting synergistically with glucose to inhibit $K_{ATP}$ channels.

$K+_{ATP}$ Channels

In β cells changes in the ATP:ADP ratio brought about by glucose metabolism inhibit $K+_{ATP}$ channels, resulting in membrane depolarization and the activation of voltage-sensitive L-type Ca2+ channels. IL pituitary cells have abundant amounts of L-type Ca2+ channels; secretion of IL hormones is affected by maneuvers that depolarize, increase excitability, or otherwise influence voltage-regulated Ca2+ channels.

To couple the metabolic changes described herein to insulin secretion a βcell $K_{ATP}$ channel can be expressed, e.g., in GLUT2- and GK-expressing ILins cells. In pancreatic βcells, ATP sensitive potassium channels ($K_{ATP}$ channels) are a key element in the regulation of glucose-induced insulin secretion and are the target for the sulfonylureas, oral hypoglycemic agents widely used in the treatment of NIDDM. Indeed, if β cells were not equipped with $K+_{ATP}$ channels, they might be tonically active and constantly releasing its insulin into the circulation regardless of the glucose concentration.

It has been shown that $K+_{ATP}$ channels are comprised of two subunits: Kir6.2, an inward rectifier K channel and SUR, the high-affinity sulfonylurea receptor, a member of the ATP-binding cassette superfamily with multiple transmembrane-spanning domains and two potential nucleotide-binding sites. Together, SUR and Kir6.2 form a potassium-selective channel ($K_{ATP}$) that modulates the membrane potential of β-cells in response to metabolically driven changes in ATP. Neither SUR nor Kir6.2 are expressed at significant levels in the pituitary.

The transfection of Kir6.2 and SUR into heterologous cells, i.e., monkey kidney (COS) cells, produces a novel potassium current with the properties expected for the β-cell $K_{ATP}$ channel, including reconstitution of an inwardly rectifying K conductance of 76 pS that was sensitive to ATP and was inhibited by sulfonlyureas and activated by diazoxide.

Thus, a cell of the invention, e.g., an intermediate lobe pituitary cell, can include an engineered nucleic acid which promotes the expression of e.g., encodes, an ion channel which mediates glucose stimulated insulin release.

In preferred embodiments the ion channel is a potassium channel, e.g., a $K+_{ATP}$ channel, e.g., the sulfonylurea receptor/Kir 6.2 channel.

Administration

The cells administered to a subject in methods of the invention can be autologous cells, allogeneic cells, or xenogeneic cells. Autologous cells can be taken from the subject, engineered, for example by retroviral insertion to express the desired gene constructs, and reintroduced into the subject. Allogeneic cells or xenogeneic cells can similarly be engineered for example by retroviral insertion of the desired genes. Transgenic animals, for example transgenic swine, can also provide a source of engineered cells for transplantation.

The present invention is also directed to a method of providing a glucose-responsive insulin-secreting capability to a mammal in need of such capability. The method includes implanting engineered cells which secrete insulin in response to glucose into such a mammal. Although cells of the invention are immunoprivileged it may be desirable to enclose or encapsulate them in an immunoisolating coating. Techniques presently in use for the implantation of islets will be applicable to implantation of cells engineered in accordance with the present invention. One method involves the encapsulation of engineered cells in a biocompatible coating. In this approach, cells are entrapped in a capsular coating that protects the encapsulated cells from immunological responses. A preferred encapsulation technique involves encapsulation with alginate-polylysine-alginate or other permselective membranes including polymers.

EXAMPLES

In the examples below, insulin expression was targeted, using transgenic mouse techniques, to proopiomelanocortin (POMC)-expressing pituitary cells in NOD mice. It has been demonstrated herein that the transgenic intermediate lobe pituitary cells efficiently process and secrete mature insulin via a regulated secretory pathway yet, unlike insulin-producing β cells, they are resistant to immune-mediated destruction.

EXAMPLES

Example 1

Construction of a POMC-Insulin Transgene

Figure 2:
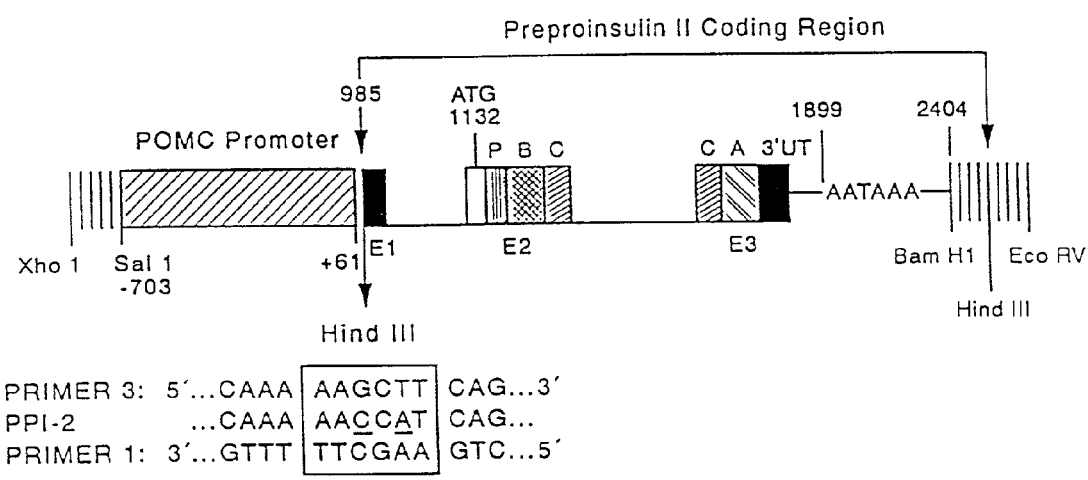

The POMC-Insulin transgene consisted of the POMC promoter region linked to the structural region of the mouse preproinsulin II (Ins) gene (FIG. 2). To excise the 5' regulatory region of the Ins gene yet preserve the translation initiation start site at position 1132, a novel Hind III restriction site was created at position 985 by site-directed mutagenesis using the recombination polymerase chain reaction (PCR) technique (Jones, D. H., Sakamoto, K., Vorce, R. L. & Howard, B. H. (1990) *Nature* (London) 344, 793–794). A 2.4 Kb genomic Bam HI Ins fragment (Wentworth, B. M., Schaefer, I. M., Villa-Komaroff, L. & Chirgwin, J. M. (1986) *J. Mol. Evol.* 23, 305–312) was cloned into pBluescript (pBS, Stratagene). The recombinant Ins-pBS vector was linearized in two separate restriction enzyme digestion reactions with Bal I (position 846) and PfiM I (position 1237). These templates were then amplified in two separate PCR reactions using primer 3:5'-CAATCAAAAGC TTCAGCAAGCAGGAAGGTAC-3' (SEQ ID NO:1) (corresponding to sense nucleotides 977–1008, mutagenesis sites underlined, region of complementarity to primer 3 in italic) and primer 2:5'-TCG TGT AGA TAA CTA CGA TAC G-3,' (SEQ ID NO:3), corresponding to nucleotides 2050–2071 of pBS. The PfiM I template was amplified with primer 1:5'-GCTGAAGCTTTTTGATTGTAGCGGATCA CTTAG -3' (SEQ ID NO:2) (corresponding to antisense nucleotides 994–962, mutagenesis sites underlined, region of complementarity to primer 1 in italic) and primer 4 (the entire primer 4 was complementary to primer 2). The PCR products were mixed together and cotransfected into bacteria. The Bal I/PfiM I fragment of a plasmid containing the Hind III mutation was then ligated into Ins-pBS that had not undergone PCR amplification. DNA sequencing of the PCR-amplified Hind III/PfiM I region did not reveal any cloning artifacts or polymerase errors.

By successive ligations, the Hind III Ins structural gene and the POMC promoter [position −703 bp to position +61 bp] (Tremblay, Y., Tretjakoff, I., Peterson, A., Antakly, T., Zhang, C. X. & Drouin, J. (1988) *Proc. Natl. Acad. Sci. USA* 85, 8890–8894) were subcloned into pBS. This promoter region has previously been shown to confer cell-specific expression and correct hormonal regulation in anterior and intermediate lobe cells of transgenic mice (Tremblay, Y., Tretjakoff, I., Peterson, A., Antakly, T., Zhang, C. X. & Drouin, J. (1988) *Proc. Natl. Acad. Sci. USA* 85, 8890–8894; Hammer, G. D., Fairchild-Hundtress V., Low, M. J. (1990) *Mol Endocrinol* 4:11 1689–1697).

Example 2

Generation of the NOD Transgenic Mice

The POMC-Ins fusion gene cassette was excised from pBS by digestion with Xho I/Eco RV (FIG. 2). The cassette was purified for microinjection and was microinjected directly into the pronuclei of one-cell embryos of NOD mice (Lipes, M. A., Rosenzweig, A., Tan, K.-N., Tanigawa, G., Ladd, D., Seidman, J. G. & Eisenbarth G. S. (1993) *Science* 259 1165–1169). Founders were identified by PCR and Southern blot analysis of tail DNA. One transgenic NOD line (POMC-Ins1) was studied in detail and is described herein.

Example 3

Expression of Insulin in the Pituitaries of Transgenic NOD Mice

Northern blot analysis of RNA from pituitary cells revealed an abundant 550 bp insulin transcript, identical in size to the endogenous pancreatic insulin transcript. In contrast, RNA from transgenic hypothalamus, brain, thymus, spleen, lymph nodes, testes, kidney, liver and salivary gland failed to show insulin signal. Immunocytochemistry of the pituitaries from the transgenic animals showed that a small percentage of cells in the anterior lobe and the great majority of cells in the intermediate lobe stained positive for insulin, similar in distribution to ACTH immunostaining. The posterior pituitary was devoid of specific insulin immunostaining and showed background signals similar to non-transgenic control pituitaries. Colocalization of insulin and ACTH (or POMC) immunoreactivity to the same pituitary cells was demonstrated by double immunolabelling the same frozen section. The ACTH antibody used in these studies was raised against the entire ACTH molecule (i.e., 1–39) and would thus be expected to recognize its cleavage products, α-MSH (ACTH 1–13) and corticotropin-like intermediate lobe peptide (CLIP, ACTH 18–39) that are present in the intermediate lobe.

To further characterize transgene expression, insulin content of the anterior and intermediate lobes and the pancreas of 6 week old transgenic NOD mice were measured by acid ethanol extraction followed by radioimmunoassay (RIA). These studies revealed that the great majority of the pituitary-derived insulin was made in the intermediate lobe with immunoreactive insulin content averaging 0.56±0.05 µg per intermediate lobe (n=5), compared to only 0.02 µg of immunoreactive insulin per anterior lobe (n=5). In contrast, pancreatic insulin content in young NOD mice averaged 23.7±0.9 µg/gland (n=5). To ascertain whether the transgenic insulin was secreted into the circulation, a 48-hour fast was performed. Since pituitary cells lack key elements of the glucose sensing apparatus including the glucose transporter GLUT-2, insulin secreted from the pituitary would not be expected to respond to ambient glucose levels (Hughes, S. D., Johnson, J. H., Quaade, C. & Newgard, C. J. (1992) *Proc. Natl. Acad. Sci. USA* 89, 688–692). Indeed, with a 60% drop in blood glucose in control NOD mice during the fast (from 112±6.0 to 46±1.6 mg/dl), serum insulin levels fell below the detection limits of the radioimmunoassay (n=12). In contrast, despite similar drops in blood glucose levels in heterozygous and homozygous transgenic mice (from 102±7.6 to 41±2.2 and 107±7.4 to 43±1.0, respectively), serum insulin levels after the 48-hour fast were markedly elevated, averaging 43.3±4.2 (n=8) and 94.6±8.6 µU/ml (n=8), respectively. These in vivo data demonstrate that the ectopically produced insulin was secreted into the circulation.

The experiments described above were performed essentially as follows. RNA Blot (Northern) Analysis. Total cellular RNA was isolated with RNAzol (Biotecx) and Northern blot analysis was performed as described previously (Lipes. M. A., Rosenzweig, A., Tan, K.-N., Tanigawa, G., Ladd, D., Seidman, J. G. & Eisenbarth G. S. (1993) *Science* 259 1165–1169). The blots were hybridized sequentially with $^{32}$P-labeled insulin and actin probes.

Immunohistochemistry was reformed essentially as follows. For paraffin sections, whole pituitaries were fixed in 10% buffered formalin at 4° C. overnight. Four micron-thick sections were stained with hematoxylin and eosin and immunostained with rabbit anti-human (1–39) ACTH (1:2, Biomeda) guinea pig anti-insulin (1:200, Incstar with a goat anti-guinea pig (1:200, Linco) as secondary antibody, followed by rabbit PAP (1:200, Dako). For plastic sections, pituitary and islet grafts were fixed overnight in Bouins' fixative, then washed and stored in 10% buffered formalin until they were embedded in plastic (Araldite; Ernest F. Fullan, Inc.). One micron-thick sections were affixed to glass by heat; the plastic resin was removed by sodium metoxide. Immunoperoxidase staining was performed with a 1:200 guinea pig anti-human insulin; a 1:3,000 cocktail of antibodies to glucagon, somatostatin, and pancreatic polypeptide (gift of Dr. Michael Appel) or rabbit anti-human ACTH [(1–39) Biomeda). Primary antibodies were incubated at 4° C. for 12 hours (ACTH) or for 48 hours (insulin and cocktail).

For frozen sections, pituitaries were fixed in 4% paraformaldehyde in PBS at 4° C. overnight. Tissues were cryoprotected in increasing concentrations of sucrose (10%, 15% and 20%) in PBS at 4° C. and embedded in tissue Tec OCT. Pituitaries were sectioned at −20° C. onto S-P Brand Superfrost Plus glass slides (Baxter Diagnostics Inc). Sections were co-incubated with guinea pig anti-human insulin (Incstar, 1:800) and rabbit anti-porcine ACTH (1:150) antisera overnight at 4° C. Primary antibodies were detected with goat anti-guinea pig IgG-Cy3 (Sigma, 1:200) and goat anti-rabbit IgG-FITC (Sigma, 1:50).

Example 4

Proinsulin is Efficiency Processed to Insulin Via a Regulated Pathway of Secretion in Transgenic Intermediate Lobe Pituitary Cells To examine the molecular forms of insulin synthesized and secreted by the transgenic intermediate lobe pituitaries and to determine whether, characteristic of regulated secretory cells, secretion in the intermediate lobe pituitaries would be coupled to extracellular stimuli, primary intermediate lobe pituitary cultures were established from the transgenic animals. Intermediate lobe pituitary cells were labeled for 15 hr with $^{35}$S-methionine, washed, and the insulin forms secreted in response to the secretagogues forskolin and IBMX during subsequent chase periods was identified by immunoprecipitation followed by alkaline urea-PAGE gel electrophoresis. These studies showed that, similar to proinsulin processing in normal islets, little insulin was detectable in the media in the basal state, but secretion was greatly enhanced in response to forskolin and IBMX. The predominant secretory product in the media of transgenic intermediate lobe pituitary cells was mature insulin. Thus, similar to islet β cells, intermediate lobe pituitary cells efficiently process proinsulin to mature insulin via the regulated pathway of protein secretion.

Metabolic labeling of freshly isolated pancreatic islets and primary cultures of transgenic pituitary cells was performed essentially as follows. Transgenic intermediate lobe pituitary tissue was digested in M-199 containing 1 mg/ml collagenase and 0.5 mg/ml type IV hyaluronidase at 37° C. Pituitary cell clusters >10–20 µM were hand-picked, washed, and placed in M-199 with 10% fetal bovine serum and Pen/Strep at 37° C. After 72 hours, the primary pituitary cell cultures were washed with methionine-free RPMI 1640 medium and radiolabelled with 0.4 mCi of L-[$^{35}$S]methionine for 15 hours in the same medium containing 10 mM L-leucine and 10% fetal bovine serum. After removal of the radiolabelled media the cells were washed with 2.0 ml of modified Krebs-Ringer bicarbonate buffer containing 20 mM Hepes, 0.1% bovine serum albumin and 11 mM glucose, and incubated for 30 min in 500 µl of the same medium at 37° C. The medium was removed and the cells were incubated for 90 minutes first in the same medium ("basal") and then in the same medium containing 1 mM forskolin and 1 mM 2-isobutyl-1-methylxanthine ("stimulated"). At the end of each incubation period the medium was removed and placed at −20° C. pending analysis.

One hundred pancreatic islets, isolated from Sprague Dawley rats, were radiolabeled for 15 hours in methionine-free RPMI 1640 medium containing 11 mM glucose, 2 mM leucine, 10% fetal bovine sera and 0.25 mCi [$^{35}$S]methionine. Following this incubation period, the medium was removed and the islets then placed in 1 ml modified Krebs-Ringer bicarbonate buffer containing 2 mM methionine, 2.8 mM glucose, 20 mM Hepes and 0.1% BSA. After a 90 minute preincubation period at 37° C., the medium was removed, replaced with 1 ml fresh medium and further incubated for 60 min. At the end of this incubation period this medium ("basal") was collected and placed at −20° C. The same islets were then incubated for a further 60 minutes with the same medium containing 16.7 mM glucose. This medium ("stimulated") was then removed and placed at −20° C.

Pituitary and islet cell lysates, and the media samples were then immunoprecipitated for (pro)insulin and analyzed by alkaline-urea PAGE, as previously described (Alarcon, C., Lincoln, B. & Rhodes, C. J. (1993) *J. Biol. Chem.* 268, 4276–4280).

Example 5

Insulin-producing Intermediate Lobe Pituitary Cells are Resistant to Autoimmune Attack Insulin has been implicated as an autoantigen in IDDM (Wegmann, D. R., Norbury-Glaser, M. & Daniel, D. (1994) *Eur. J. Immunol.* 24, 1853–1867; Eisenbarth, G. S. (1994) *Diabetes Care* 17(6), 605–607). However the expression of insulin in the pituitary, which is not normally involved by autoimmunity in NOD mice, did not engender the development of ectopic lymphocytic infiltrates (i.e., hypophysitis). Serial examination of the pituitaries from these transgenic NOD mice (and from other POMC-Ins transgenic NOD mouse lines) failed to reveal the presence of ectopic lymphocytic infiltration, even after the onset of diabetes. To exclude the possibility that either the anatomical location of the pituitary gland or the sustained production of insulin in the transgenic NOD mice might be impairing immune responsiveness to the ectopically expressed insulin, transgenic pituitaries, and control islets, were transplanted under the kidney capsules of "naive" (nontransgenic) overtly diabetic NOD recipients. When control islet grafts were removed from the kidney capsule of the recipients two weeks after transplantation, the grafts showed severe infiltration with complete loss of the insulin-staining β cells, with only non-β cells remaining. In striking contrast, the transgenic pituitary grafts, placed under the capsule of the contralateral kidney, were devoid of lymphocytic infiltration and showed abundant staining for insulin and ACTH. Thus the ectopic expression of insulin in the pituitary did not elicit the development of pathologic lesions.

One possible explanation for these findings was that in the absence of antecedent cell injury or of a "triggering event" similar to that which leads to insulitis, the transgenic pituitaries might not contain sufficient numbers of antigen presenting cells to activate the relevant lymphocytes to effect destruction of the insulin-expressing pituitary cells. To address this concern, and to examine the relative ability of the intermediate lobe pituitary cells to withstand inflammatory damage, islet and transgenic pituitary cells were mixed together and engrafted into a single site under the kidney capsules of diabetic NOD mice. This resulted in the development of severe lymphocytic infiltration over the entire graft, including areas containing pituitary tissue. Although there was complete destruction of insulin-producing β-cells in the islets, the insulin-positive cells of the pituitary remained intact. Indeed, the only insulin-positive cells that remained in the grafts co-localized with ACTH staining and were thus, pituitary-derived. These studies indicate that, even when placed in direct contact with islet-specific pathogenic lymphocytes (presumptively, many of which are insulin-specific (Marcinkiewicz, M., Day, R., Seidah, N. G. & Crétien, M. (1993) *Proc. Natl. Acad. Sci. USA* 90, 4) the insulin-expressing transgenic pituitaries were not susceptible to immune-mediated destruction.

Example 6

Transplantation of the Transgenic Pituitaries Cures Diabetes in NOD Mice

Figure 3:
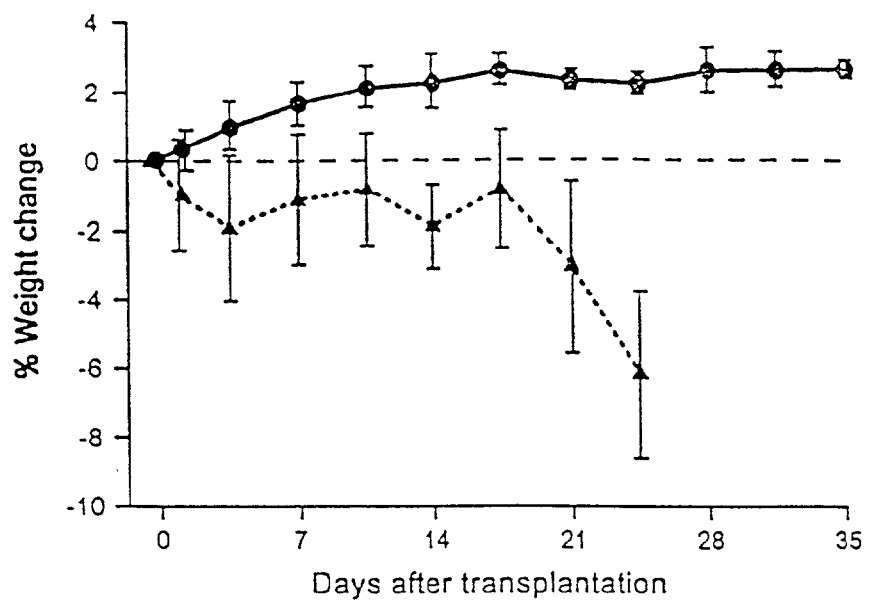
Figure 3:
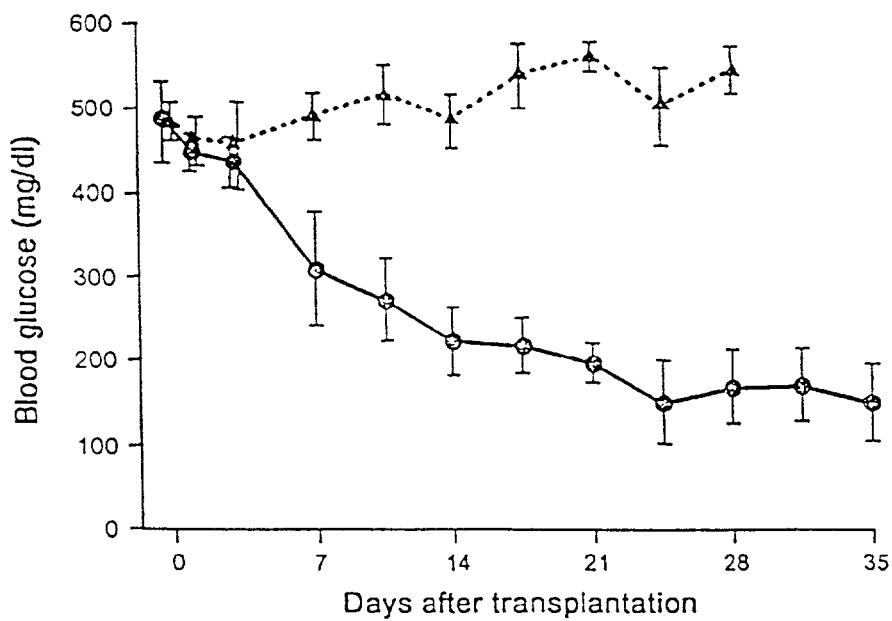

The ability of the transgenic intermediate lobe pituitary cells to efficiently process and secrete mature insulin, along with their resistance to autoimmune attack and injury, show that these cells can be used as a vehicle for insulin replacement in IDDM. Indeed, it was found that transplantation of 4 intermediate lobe pituitaries under the kidney capsule of spontaneously diabetic NOD mice resulted in a significant gain in body weight (FIG. 3A) and in the complete remission from diabetic symptoms. This was associated with the progressive return to near-normoglycemia (FIG. 3B), with mean BG levels decreasing from 484±21 mg/dl pre-transplantation to 150±43 mg/dl after transplantation (n=6). In parallel with this drop in BG, random insulin levels increased from 4±0.2 μU/ml pre-transplantation to 42±9 μU/ml post-transplantation, in a similar range to random insulin levels of nondiabetic control mice [39±9 μU/ml (n=6)]. At the end of the transplantation period, immunohistochemistry of the grafts of the recipients showed abundant insulin staining with no evidence of lymphocytic infiltration. Similar analysis of pancreatic sections from recipients did not reveal any significant insulin-positive cells, confirming that the enhanced insulin levels post-transplantation were due to the transgenic tissue implants. These results demonstrate that the intermediate pituitary-derived insulin is biologically active and are consistent with the biochemical studies which showed that the great majority of insulin secreted by the transgenic pituitaries is fully processed, mature insulin. Diabetic NOD mice receiving nontransgenic (control) intermediate lobe pituitaries had no reduction in serum BG levels, and had increasingly severe diabetic symptoms which resulted in their demise within 3 weeks after transplantation.

The experiments described above were performed essentially as follows. Pituitary and Islet Isolation and Transplantation: Islets were obtained from young (<6 week) female homozygous POMC-Ins1 transgenic NOD mice by collagenase infusion of the pancreas through the common bile duct as described (Gotoh, M., Maki, T., Kiyoizumi, T., Satoim, S. & Monaco, A. P. (1985) *Transplantation* 40, 1715–1720) Aliquots of 100 islets (>75 and <250 μM in diameter) were hand-picked under a stereomicroscope. Intermediate lobe pituitaries from transgenic female NOD mice diced into fragments <250 μM. Grafts consisted of 100 islets placed under the capsule of the kidney and the diced transgenic intermediate lobes placed under the contralateral kidney capsule; or 100 islets mixed with the transgenic intermediate lobe fragments placed into a single site under the kidney capsule. Recipients consisted of diabetic (BG levels >350 mg/dl for at least 1 week) female NOD mice. Two weeks after transplantation, the grafts were visualized under a stereomicroscope, excised and fixed in Bouins' for histological processing.

For the therapeutic transplantations, diabetic female NOD mouse recipients (n=6) were transplanted under the kidney capsule with 4 diced intermediate lobe transgenic pituitaries. The control group consisted of diabetic female NOD mice (n=3) transplanted with 4 diced intermediate lobes from nontransgenic NOD mice. After transplantation, mice were followed with serial blood glucose analyses using a One Touch II meter (Lifescan) and body weights. Five weeks after transplantation, mice were sacrificed and their grafts were fixed in Bouin's for histological examination.

Examples 1–6 describe the generation of transgenic NOD mice in which insulin expression was targeted to POMC-expressing cells of the pituitary. It is shown that, similar to islet β cells, the POMC-expressing intermediate lobe pituitary cells from transgenic mice efficiently process proinsulin to mature, biologically active insulin via a regulated pathway of protein secretion. Unlike pancreatic β cells, however, the insulin-expressing pituitary cells are not immunologically attacked in diabetic NOD mice. Indeed, transplantation of the transgenic intermediate lobe pituitary tissues into spontaneously diabetic NOD mice restored normoglycemia and reversed diabetic symptoms. The absence of autoimmune infiltration in intermediate lobe pituitary cells engineered to secrete insulin provides in vivo evidence of the potential of these cell types for gene replacement therapy in IDDM.

Example 7

Primary Cultures of Insulin Secreting Intermediate Lobe Pituitary Cells are Efficiently Transduced with Recombinant Adenovirus Recombinant adenovirus can be used study glucose sensing in β cells (see, e.g., Becker, T., Beltrandelrio, H., Noel, R., Johnson, J. & Newgard, C., (1994) *J. Biol. Chem.*

269(33): 21234–21238; Becker, T., Noel, R., Coats, W., Gomez-Foix, A., Alam, T., Gerard, R. & Newgard, C.: (1994) *Methods in Cell Biol* 43: 161–189) and hepatocytes (see, e.g., Gomez-Foix, A. M., Coats, W. S., Baque, S., Alam, T., Gerard, R. D. & Newgard, C. B.: (1992) *J. Biol. Chem.* 267:25129–34; O'Doherty et al., 1996). The feasibility of using adenovirus gene delivery in primary cultures of intermediate lobe pituitary cells is shown by the following experiments. Intermediate lobe pituitary cells were treated with AdCMV-βgal, an Ad5 recombinant virus containing the human cytomegalovirus immediate-early promoter (CMV) and a nuclear-localizing variant of the *Escherichia coli* β-galactosidase reporter gene (βgal) in place of the E1 sequences and a deletion in the E3 region. Transduction of intermediate lobe pituitary cells with AdCMV-βgal demonstrated gene transfer to intermediate lobe pituitary cells with high efficiency (>95% of total cells), as assessed by counting the number of blue cells and dividing by the total number of cells in multiple sections. Intermediate lobe tissues are known to contain a very homogeneous population of cells with approximately 98% of cells being POMC-expressing melanotrophs (Chronwall, B., Millington, W., Griffin, W. S., Unnerstall, J. & O'Donohue, T.: (1987) *Endocrinology* 120:1201–1211). Thus it is likely the great majority of the cells of the interest took up virus. Intermediate lobe cells that were not treated with AdCMV-βgal did not contain any blue cells, even after prolonged incubation with the β galactosidase substrate. This efficiency is similar to that achieved in primary hepatocytes (Gomez-Foix, A. M., Coats, W. S., Baque, S., Alam, T., Gerard, R. D. & Newgard, C. B.: (1992) *J. Biol. Chem.* 267:25129–34).

To definitively demonstrate that the insulin-expressing intermediate lobe pituitary cells efficiently take up adenovirus, primary cultures of intermediate lobe pituitary cells from POMC-ins transgenic mice were transduced with recombinant adenovirus containing a human growth hormone (GH) cDNA reporter gene (AdCMV-GH). Hormonal colocalization studies were then performed by double immunofluorescence staining of the same slide. Since GH-producing cells are never normally present in the IL, the detection of GH-positive IL cells is a highly specific assay for adenovirus infection. For these studies, primary cultures of ILins cells were established on Flaskette chamber culture slides (Nunc). Two weeks later, each chamber containing ~1×10$^6$ cells, was transduced with AdCMV-GH (at a titer of ~3×10$^9$ pfu/ml). Four days later, the slides were rinsed, fixed in 10% buffered formalin and incubated with a mixture of antibodies to human GH (obtained from the NIDDK Pituitary Program) and insulin (Linco), followed by a mixture of secondary antibodies labeled with FITC (GH) and Cy3 (insulin). These studies showed that GH and insulin immunoreactive staining colocalized in the same IL cells, with virtually all of the insulin-positive cells co-expressing the virally introduced growth hormone reporter gene. As expected, there was no specific GH staining in ILins cells that were not transduced with AdCMV-GH. These results demonstrate the feasibility of using recombinant adenovirus vectors to deliver genes, e.g., genes to be evaluated for their effect on glucose sensing, to IL cells.

Example 8

GLUT-1, GLUT-2, and Glucokinase Expression in Intermediate Lobe Pituitary Cells

To evaluate the metabolic machinery present in IL cells, the expression of a number of components implicated in glucose sensing was examined by Northern blot analysis and expression levels to liver, brain, lung, stomach, the islet β cell-derived, glucose-responsive (murine) cell line MIN6, and anterior lobe (AL) of the pituitary were compared.

When the blot was probed with $^{32}$P-labeled cDNA probe encoding GLUT-2, the high $K_m$ liver/islet glucose transporter, large amounts of transcripts were present in liver and stomach; with smaller amounts in MIN6 cells. GLUT-2 mRNA was not expressed in the AL, consistent with previous reports (Hughes, S. D., Quaade, C., Milburn, J. L., Cassidy, L. & Newgard, C. B.: (1991) *J. Biol. Chem.* 266:4521–4530.; Liang, Y., Jetton, T., Zimmerman, E., Najafi, H., Matschinsky, F. & Magnuson, M.: (1991) *J Biol Chem* 266(11): 6999–7007) or the IL. High levels of the low $K_m$ erythroid/brain glucose transporter GLUT-1 were expressed in IL and AL of the pituitary, similar to brain.

To study glucokinase expression, the same blot was stripped and reprobed with the 660 bp DNA probe containing part of the glucokinase sequence that is common to both liver and islet glucokinase. A glucokinase transcript of 2.4 kb was present in liver as well as in stomach, while a larger glucokinase transcript of 2.8 kb was abundant in AL and IL pituitary tissues, similar to levels in control β cells (MIN6 cells). Previous studies have shown that the pituitary and islets use a common promoter and share an mRNA-splicing pathway that is distinct from that leading to the production of the smaller 2.4 kb transcript in the liver (Liang, Y., Jetton, T., Zimmerman, E., Najafi, H., Matschinsky, F. & Magnuson, M.: (1991) *J Biol Chem* 266(11): 6999–7007).

Stomach tissue expresses high levels of GLUT-2 and the liver isoform of glucokinase. It has been shown in transgenic mice that the glucokinase promoter is expressed in the gastric antrum but that, surprisingly, glucokinase expression did not localize to gastric or other neuroendocrine cell types (Jetton, T. L. & Magnuson, M. A.: (1992) *Proc. Natl. Acad. Sci. USA* 89:2619–2623). Further hybridization of the same blot with an insulin probe showed abundant insulin mRNA in MIN6 cells and the IL tissue (derived from transgenic NOD mice), following a 2 hour exposure.

To examine whether immunoreactive glucokinase protein was present in intermediate lobe cells, Western blot analysis was performed using the sheep anti-rat glucokinase antiserum that was raised against the common regions of the liver and islet glucokinase polypeptide (Jetton, T. L. & Magnuson, M. A.: (1992) *Proc. Natl. Acad. Sci. USA* 89:2619–2623). Both anterior and intermediate lobes of the pituitary cells produced a ~52 kDa GK polypeptide that was similar in size and quantity to that found in control MIN6 cells. No bands were detected in experiments with pre-immune serum.

Example 9

Detection of the GLP-1R Signaling Pathway

GLP-1 is known to exert diverse insulinotropic actions on β-cells and to trigger insulin secretion in glucose-resistant β cells by interacting synergistically with glucose to inhibit $K_{ATP}$ channels (Holz, G. G., Kuehtreiber, W. M. & Habener, J. F.: (1993) *Nature* 361:362–365). As previously discussed, GLP-1 is synthesized not only in the gut but in the brain, and specific, high affinity receptors for GLP-1 ($k_d$~4 nM) are present in the pituitary, although at considerably lower abundance than in β cells (Shimuzu et al., 1987). By Northern blot analysis, probing with a rat GLP-1R cDNA, the β-cell derived MIN6 cells expressed abundant amounts of GLP-1R mRNA, whereas there was no detectable GLP- 1R transcripts in pituitary cells. However, GLP-1R mRNA was detected in the AL and IL of the pituitary by RT-PCR analysis, using GLP-1R specific primers. These results indicate that the GLP-1R is expressed at low levels in the IL pituitary.

Example 10

Creation of Recombinant Adenovirus Containing GLUT-2, Glucokinase and the GLP-1 Receptor The effect of the expression of a nucleic acid sequence on glucose-stimulated insulin secretion can be tested by introducing a candidate component into a primary culture of insulin-secreting IL cells (ILins) using adenovirus gene transfer vectors. Adenovirus mediated gene transfer into intermediate lobe pituitary cells is highly efficient. Adenovirus has been shown to infect >95% of the IL pituitary cells in a culture, as determined by β-galactosidase staining. Furthermore, adenovirus infected virtually all of the insulin-producing intermediate lobe pituitary endocrine cells.

The recombinant adenoviruses can use the bacteriophage-derived Cre-loxP recombination system (Hardy S. et al., *J. Virol.* 1997, March 71(3):1842–9). In this system, Cre recombinase is useful in both creating recombinants and selecting against the starting helper virus. The selection is based on the finding that deleting a ~150 bp sequence in the left-most end of the virus prevents the viral chromosome from being packaged into capsids. There are three unique interacting components in this system. The first is a modified 293 human embryonic kidney cell line, CRE8, which constitutively expresses Cre recombinase. The second is a shuttle vector plasmid pAdMDM, and the third is the ψ5 helper virus. The shuttle vector pAdMDM, is a pBluescript (pBS)-based plasmid in which the PvuII sites and the intervening sequence from positions 529 to 977 were excised and replaced with an Ad5-based portion containing a left ITR, a packaging sequence, the CMV promoter, a polylinker cloning region, followed by a polyadenylation signal from SV40, a single loxP site, and a right ITR. The ψ5 helper virus is an E1- and E3-deleted version of Ad5 containing loxP sites flanking the packaging site. In this system, the Cre recombinase (from CRE8 cells) catalyzes the removal of DNA between the loxP sites in ψ5, deleting the packaging site. Cre recombinase also catalyzes a recombination between ψ5 and pAdMDM. The new recombinant virus thus has an intact packaging site and a single loxP site, and has a considerable growth advantage over the deleted ψ5 virus.

pAdMDM shuttle vectors containing cDNAs encoding GLUT-2 (Thorens, B., Sarkar, H. K., Kaback, H. R., Lodish, H. F.: (1988) *Cell* 55:281–290), the islet isoform of glucokinase, GK.B1 (Liang, Y., Jetton, T., Zimmerman, E., Najafi, H., Matschinsy, F. & Magnuson, M.: (1991) *J Biol Chem* 266(11): 6999–7007) and the GLP-1R (Thorens, B.: (1992) *Proc. Natl. Acad. Sci. USA* 89:8641–8645) were prepared. The 1.7 Kb Xba-SmaI GLUT-2 cDNA fragment was ligated into the XbaI-Sal I site of pAdMDM, after filling in its Sal I recessed end with the Klenow fragment of DNA polymerase I. The KpnI-XbaI GK.B1 cDNA fragment which was excised from the pCMVGK.B1 plasmid (Liang, Y., Jetton, T., Zimmerman, E., Najafi, H., Matschinsy, F. & Magnuson, M.: (1991) *J Biol Chem* 266(11): 6999–7007) was cloned into the EcoRI-XbaI site of pAdMDM, after converting the recessed ends of KpnI and EcoRI into blunt ends by treatment with the Klenow fragment; and the BamHI-XhoI GLP-1R cDNA fragment was cloned directly into the BamHI-XhoI site of pAdMDM. The GLUT-2-pAdMDM and the GK.B1-pAdMDM vectors were then cut with the restriction endonuclease SfiI; because the GLP-1R sequence contains an SfiI site, the recombinant GLP-1R-pAdMDM was cut with DrdI (like SfiI, this enzyme cuts twice in the plasmid). CRE8 cells were co-transfected with the recombinant plasmids and the ψ5 helper virus by calcium coprecipitation.

The recombinant adenoviruses (Ad-GLUT-2; Ad-GK.B1 and Ad-GLP-1R) were expanded on 293 cells and high-titer stocks prepared by CsCl centrifugation according to standard procedures (Becker et al., 1994).

Example 11

Expression of the Recombinant Viral Vectors in Primary Cultures of Intermediate Lobe Pituitary Cells The GLUT-2, GK.B1, and $K+_{ATP}$ channel recombinant adenoviruses can be transduced separately and in combination into 4-day-old primary cultures of ILins cells. Primary cultures of ILins cells can be prepared from the POMC-ins transgenic NOD mice by enzymatic dispersion of the IL tissues into individual cells as previously described (Lipes, M. A., Cooper, E. M., Skelly, R., Rhodes, C. J., Boschetti, E., Weir, G. C. & Davalli, A. M.: (1996) *Proc. Natl. Acad. Sci. USA* 93: 8595–8600). Each mouse intermediate lobe contains about $2.0 \times 10^5$ cells. The cells will be maintained at a density of one intermediate lobe pituitary cell per well in 24-well plates (Costar) in RPMI supplemented with 10% FBS and 200 units/ml penicillin, and 200 μg/ml streptomycin. Four days after plating the ILins cells, they will be infected with 200 l of media containing 10×multiplicity of infection ($2.0 \times 10^6$ pfu) of recombinant adenoviruses, or control virus (AdCMV-βgal) for 2 hours at 37° C. Four days later after transduction, expression of each of the introduced genes will be assessed.

Example 12

Assays of Transgenic Expression

GLUT-2, GK.B1, and $K+_{ATP}$ channel expression levels in IL pituitary cells can be measured by Western blot analysis and the expression levels compared to normal mouse islets. GLUT-2 expression can be detected using a rabbit anti-rat carboxyl-terminal 25-mer GLUT-2 peptide antiserum (1:500 dilution, Acres Biologicals). GK.B1 expression can be assessed using sheep anti-rat GK antiserum. The bound antibodies can be visualized with a horseradish peroxidase-conjugated secondary antibody and a chemiluminescent substrate (ECL, Amersham) by exposure to an x-ray film and quantitated by densitometry. Protein samples in separate lanes will be stained with Coomassie blue, and the dried gel will be quantitated by densitometry to normalize for protein loading. Immunolocalization of GLUT-2, GK and GLP-1 can be carried out by indirect immunofluorescent staining of frozen pituitary sections,.

Example 13

Functional Assays of Transgene Expression

A. GLUT-2: Glucose transport measurements in the GLUT-2/insulin expressing intermediate lobe cells, control AdCMV-βgal IL cells, and control islets can be assayed by 3-O-methylglucose uptake under zero-trans conditions, see, e.g., Araki et al., 1994 and Johnson et al., 1990. Initial velocities of uptake can be derived from measurements at 3, 15 and 30 seconds, based on similar studies on AtT20 anterior pituitary cells (Hughes, S. D., Johnson, J. H., Quaade, C. & Newgard, C. J.: (1992) *Proc. Natl. Acad. Sci. USA* 89:688–692.). The Eadie-Hofstee plot can be used to analyze the kinetics of 3-O-methyl-D-glucose uptake. Glucose transport in the mock transfected (AdCMV-βgal) control intermediate cells should be minimal, whereas the $K_m$ and $V_{max}$ values for glucose transport in the GLUT-2 expressing cells should be similar to islets (Hughes, S. D., Johnson, J. H., Quaade, C. & Newgard, C. J.: (1992) *Proc. Natl. Acad. Sci. USA* 89:688–692.). Another way of assessing functional GLUT-2 expression is to assess whether the engineered IL cells become susceptible to the toxic effects of streptozotocin (STZ). It has been shown in transfected cell lines that STZ has a potent cytotoxic effect on cells expressing GLUT-2, but not on cells expressing GLUT-1; i.e, only GLUT-2-expressing cells were found to transport STZ efficiently (Schnedl et al., 1994). The i.p. injection of 200 mg/kg STZ into mice harboring insulin secreting transgenic IL pituitary grafts resulted in severe β-cell destruction, whereas the IL pituitary grafts remained intact with no evidence of tissue damage. The enhanced toxic effects of STZ can be assessed by administering the identical STZ dosage (200 mg/kg i.p.) to the mice harboring intermediate lobe grafts that have been bioengineered to express GLUT-2. The cytotoxic effects will be assessed by examining the grafts for evidence of cellular destruction and by immunostaining with GLUT-2 and insulin antisera.

B. Glucokinase: Glucose phosphorylating activity can be determined by the fluorometric method as previously described (Trus, M. D., Zawalich, W. S., Burch, P. T., Berner, D. K., Weill, V. A. & Matschinsky, F. M.:(1981) *Diabetes* 30:911–922; Liang, Y., Jetton, T., Zimmerman, E., Najafi, H., Matschinsy, F. & Magnuson, M.: (1991) *J Biol Chem* 266(11): 6999–7007). Assays can be performed 4 days after transduction of the recombinant adenovirus. Although low levels of glucokinase activity (20–30% of the activity in normal islets) have been detected in certain sublines of AtT20 tumor cells (Hughes, S. D., Quaade, C., Milburn, J. L., Cassidy, L. & Newgard, C. B.: (1991) *J. Biol. Chem.* 266:4521–4530.), glucokinase activity is undetectable in primary anterior pituitary extracts (Liang, Y., Jetton, T., Zimmerman, E., Najafi, H., Matschinsy, F. & Magnuson, M.: (1991) *J Biol Chem* 266(11): 6999–7007; Hughes, S. D., Quaade, C., Milburn, J. L., Cassidy, L. & Newgard, C. B.: (1991) *J. Biol. Chem.* 266:4521–4530). Thus, little, if any, glucokinase activity should be present in vector control transfected IL cells but that activity should be greatly enhanced with introduction of the cDNA encoding the islet isoform of glucokinase, GK.B1 (Liang, Y., Jetton, T., Zimmerman, E., Najafi, H., Matschinsy, F. & Magnuson, M.: (1991) *J Biol Chem* 266(11): 6999–7007). Trypsinized pituitary cells ($4\times10^5$) and freshly isolated mouse islets (~250 islets, to be obtained from the Islet Provision Core) will be washed free of glucose and homogenized in a buffer containing 20 mM $K_2HPO_4$, 5 mM DTT, 1 mM EDTA, 110 mM KCL. Homogenized intermediate lobe pituitaries and islets will be centrifuged at 4° C. for 30 min at 12,000×g. The supernatant fraction will be used for glucokinase and hexokinase determination. An aliquot of supernatant will be removed to determine total protein concentration. Supernatant (1–5 μl) will be added to 100 μl of buffer containing 50 mM Hepes, pH 7.6, 100 mM KCl, 7.4 mM $MgCl_2$, 15 mM β-mercaptoethanol, 0.5 mM $NAD^+$, 0.05% bovine serum albumin, 0.70 unit/ml glucose-6-phosphate dehydrogenase from *Leuconostoc mesenteroides* (Boehringer Mannheim), 5 mM ATP, and varying concentrations of glucose (0.03, 0.06, 0.125, 0.25, 0.5, 6, 12, 24, 60 and 100 mM). The mixture will be incubated at 30° C. for 90 min. The reaction will then be terminated by adding 1 ml of 0.5 mM $NaHCO_3$, pH 9.4, and NADH fluorescence will be measured on a Ferrand Ratio-2 Fluorometer (in the Section on Metabolism laboratory at the Joslin Diabetes Center). The $V_{max}$ and $K_m$ values for glucose will be determined by analyzing the data with Eadie-Hofstee plots.

C. GLP-1 Receptor: A large body of evidence indicates that GLP-1 exerts its effects on β cells by stimulating the production of cAMP (Holz, G. G., Kuehtreiber, W. M. & Habener, J. F.: (1993) *Nature* 361:362–365). Insulin secretion in IL pituitary cells is markedly enhanced by agents that increase intracellular cAMP such as forskolin and IBMX (Lipes, M. A., Cooper, E. M., Skelly, R., Rhodes, C. J., Boschetti, E., Weir, G. C. & Davalli, A. M.: (1996) *Proc. Natl. Acad. Sci. USA* 93: 8595–8600). To confirm that GLP-1 also acts in the GLP-1 receptor expressing IL pituitary cells via a cAMP-mediated signaling pathway, and that cAMP levels are increased in a dose-dependent manner, receptor-induced cAMP accumulation in cultured cells can be assessed as described (Thorens, B. & Waeber, G.: (1993) *Diabetes* 42:1219–1225). Cells can be incubated for 15 min at 37° C. in the presence of 250 μmol/l IBMX, with GLP-1 concentrations ranging from 10 pool/l to 1 μmol/l). cAMP content of acetylated samples can be measured using a $^{125}I$ cAMP radioimmunoassay kit (Amersham).

Example 14

In Vitro Evaluation of Insulin Secretion

To determine whether glucose-stimulated insulin secretion is conferred in ILins cells by genetic manipulations, in vitro perfusion studies or static incubation studies can be performed. Static incubation studies are described in Hughes, S. D., Quaade, C., Milburn, J. L., Cassidy, L. & Newgard, C. B.: (1991) *J. Biol. Chem.* 266:4521–4530. Approximately $2\times10^5$ IL cells (corresponding to one IL pituitary/well) grown on 24-well plates (Costar) can be incubated for an additional 24 h in DMEM media supplemented with 1 mM glucose. Cells can then be washed twice in glucose-free HBSS with 1% FBS. Glucose-stimulated insulin secretion will be measured in four independent wells by incubating the cells at 37° C. for 2 h in HBSS alone (no secretagogues), HBSS+glucose (0.1, 2.5, 5, 10 and 20 mM) or, as a control for insulin secretion, HBSS+5 μM forskolin and 1 mM isobutylmethylxanthine (IBMX). This combination of forskolin and IBMX should exert a 8–10 fold stimulatory effect on insulin release in IL pituitary cells.

In normal islets, glucose potentiates the insulin secretory response to various cell secretagogues, including agents that increase intracellular cAMP levels (Ullrich, S. & Wolheim, C.: (1984) *J Biol Chem* 259: 4111–4115). To assess whether glucose potentiates the secretory response to non-glucose secretagogues in genetically modified ILins cells, these cells can be incubated with 0.5 μM forskolin or 0.5 μM forskolin plus 2.5 mM glucose for a period of 3 hr, as described (Hughes, S. D., Johnson, J. H., Quaade, C. & Newgard, C. J.: (1992) *Proc. Natl. Acad. Sci. USA* 89:688–692.). For all of these experiments, the medium will be centrifuged at 1,000×g, and stored at −20° C. until the insulin assays are performed. Insulin content of the cells will be measured by washing the wells with PBS and then adding 2 ml of a solution containing 74% ethanol and 1.4% HCL. The plates will then be stored at −20° C. overnight, after which the supernatants will be collected and stored at −20° C. Insulin levels in the medium and cell lysate will be measured by radioimmunoassay using rat insulin standards and normalized to protein content/well.

To assess whether the administration of GLP-1 will enhance the responsiveness of bioengineered cells to glucose, glucose responsiveness in primary cultures GLP-1R expressing ILins cells in the presence or absence of the GLUT-2 and glucokinase transgenes will be compared. As has been described in β cells (Holz, G. G., Kuehtreiber. W. M. & Habener, J. F.: (1993) *Nature* 361:362–365), in the absence of glucose, very little insulin should be released into the media in response to the administration of GLP-1 (Peninsula Laboratories). However, with the addition of 10 mM glucose, GLP-1 would be expected to significantly enhance insulin secretion. Presumptively, this should only occur in the cells that have glucose-sensing capabilities, i.e., in cells that also express the GLUT-2 and/or GLUT-2/glucokinase transgenes. The timing of the application of glucose and GLP-1 can be examined to determine whether, as has been reported in glucose-resistant β cells, pretreatment with GLP-1 will render the ILins cells glucose-sensitive. Because the insulinotropic actions of GLP-1 are glucose-dependent, it may be desirable to also assess whether, conversely, GLP-1 resistant cells can be rendered glucose-sensitive by prior application of glucose (Holz, G. G., Kuehtreiber, W. M. & Habener, J. F.: (1993) *Nature* 361: 362–365). The dose-response relationship of the ability of GLP-1 to stimulate insulin secretion can be evaluated over a concentration range of 0.01–100 nM, in the presence of 10 mM glucose (Thorens, B.: (1992) *Proc. Natl. Acad. Sci. USA* 89:8641–8645).

Example 15

In Vivo Perfusion Studies

Perfusion studies can be carried out to study the dynamics of insulin release in vivo and to evaluate whether glucose-stimulated insulin secretion from the bioengineered ILins pituitary cells occurs in a concentration range (5–20 mmol/l) and in a time frame that resembles the normal islet β-cell response. Grafts will consist of GLUT-2, glucokinase and GLUT-2/glucokinase expressing IL cells from four transgenic donors, a tissue dosage previously demonstrated to reverse hyperglycemia (Lipes, M. A., Cooper, E. M., Skelly, R., Rhodes, C. J., Boschetti, E., Weir, G. C. & Davalli, A. M.: (1996) *Proc. Natl. Acad. Sci. USA* 93: 8595–8600) or equivalent amounts of bioengineered insulin producing IL cells. Recipients will consist of diabetic NOD mice. Perfusion of the graft-bearing kidneys will be performed 2 weeks after transplantation (to allow adequate time for engraftment), using previously described methods (Ogawa, Y., Noma, Y., Davalli, A. M., Wu, Y.-J., Thorens, B., Bonner-Weir, S. & Weir G. C.: (1995) *Diabetes* 44: 75–79). Anesthetized transplanted mice will be cannulated through the aorta and abdominal aorta and the renal vein using PE60 polyethylene tubing (Clay Adams) and perfused with Krebs-Ringer buffer containing glucose starting with perfusion with 5.5 mmol/l glucose for 5 min, followed by 10 min perfusion with 16.7 mmol/glucose, followed by perfusions with 5.5 mmol/l glucose, 5 mmol/l glucose with arginine and, finally, with 5 mmol/l glucose alone.

Example 16

Metabolic Assays

To determine whether the bioengineered ILins pituitary cells have features of glucose metabolism similar to normal cultured islets, the glucose concentration dependencies of glucose usage and glucose oxidation can be examined in the recombinant adenovirus transduced ILins cells and compared to mock (i.e., AdCMV-βgal) transfected ILins cells and to islets cultured for the same duration of time. Four days after administration of recombinant virus (or 4 days of culture after transduction with AdCMV-βgal) cells will be washed twice in HBSS lacking glucose and resuspended in HBSS containing 3 or 20 mM glucose. Glucose usage will be monitored by measuring the conversion 5-[$^3$H]glucose (DuPont NEN) to $^3$H$_2$O, as described (Trus, M. D., Zawalich, W. S., Burch, P. T., Berner, D. K., Weill, V. A. & Matschinsky, F. M.: (1981) *Diabetes* 30:911–922; Hughes, S. D., Quaade, C., Johnson, J. G., Ferber S. & Newgard, C. B.: (1993) *J. Biol. Chem.* 268(20):15205–12). Measurements will be performed for 15 min in a final volume of 250 μl. Glucose usage will be calculated after correction for the efficiency of equilibration with a $^3$H$_2$O standard, as described (Ashcroft, S. J. H.: (1981) *The Islets of Langerhans*. Cooperstein, S. J., Watkins, D. Eds. Academic, London, 117–48). Glucose oxidation will be determined by measuring $^{14}$CO$_2$ production from [U-$^{14}$C]glucose (DuPont NEN) incubated with 3 or 20 mM glucose for 3 h at 37° C., as described (Liang, Y., Bai, G., Doliba, N., Buettger, C., Wang, L., Berner, D. & Matschinsky, F.: (1996) *Amer Physiol Soc E*846–E857).

Example 17

Generation of Transgene Constructs for Microinjection

A POMC-GLUT-2 transgene was constructed by subcloning a 616 bp EcoRI-SalI fragment containing the intron (286 bp) and polyA element (330 bp) from the minigene pxf3, downstream from the POMC promoter (position −703 to +61) (Tremblay et al., 1988). This POMC promoter had been inserted in a Bluescript (pBS) vector in which the KpnI site in the polylinker was deleted by blunt-end conversion with Klenow enzyme treatment, followed by re-ligation. The rat GLUT-2 cDNA (Thorens, B., Sarkar, H. K., Kaback, H. R., Lodish, H. F.: (1988) *Cell* 55:281–290) was then inserted into the only remaining KpnI site, thereby placing it immediately downstream of a hybrid intron element and upstream of the SV40 late polyadenylation site. The 3 kb transgene cassette, containing, in order, the POMC promoter, a upstream hybrid intron element, the GLUT-2 cDNA, and a downstream SV40 late polyadenylation signal element was excised from pBS by digestion with EcoRV and ApaI, and was purified for microinjection. Similar strategies were used to generate the transgene constructs containing the islet isoform of glucokinase (GK.B1) and the GLP-1R.

Example 18

Generation and Maintenance of the Transgenic NOD Mouse Lines

As the expression of GLUT-2 and glucokinase are desirable for optimal glucose sensing, GLUT-2 and glucokinase transgenic mice are useful. These transgenes can be injected directly into embryos derived from matings between homozygous POMC-Ins transgenic NOD mice. Transgene status can be assessed by PCR and transgene copy number by Southern blotting of tail DNA. The transgenic lines can be maintained by mating the founders and their transgenic offspring with homozygous POMC-Ins transgenic NOD mice. GLP-1 receptor transgenic NOD mice can also be made. They can be mated with the derived GLUT-2/glucokinase transgenic mice to generate a source of insulin-producing tissue that expresses all three sensors. Microinjecting the constructs directly into embryos from POMC-ins NOD mice will enable assessment of the effects of each of these glucose sensors in the context of IL cells in which insulin expression has already been extensively characterized, both in vitro and in vivo (Lipes, M. A., Cooper, E. M., Skelly, R., Rhodes, C. J., Boschetti, E., Weir, G. C. & Davalli, A. M.: (1996) Proc. *Natl. Acad. Sci. USA* 93: 8595–8600). Co-expression of these genes in the POMC-ins mice should not present a problem, since despite having high levels insulin expression in the pituitary, the POMC-Ins line has only a single transgene copy (per chromosomal allele) by Southern blot analysis. It has been shown that expression of high copy numbers of reporter genes (75 copies) driven by this identical POMC promoter fragment did not inhibit endogenous POMC expression (Tremblay, Y., Tretjakoff, I., Peterson, A., Antakly, T., Zhang, C. X. & Drouin, J.: (1988) *Proc. Natl. Acad. Sci. USA* 85:8890–8894).

Expression levels of each of the introduced sensors can be assessed in offspring from the founders by Western blotting and immunocytochemistry.

Example 19

Assessment of the Efficacy of the Glucose-sensitive Insulin Secreting IL Tissues for β Cell Replacement in IDDM To determine the therapeutic efficacy of the genetically manipulated ILins pituitary tissues in the transplantation setting, NOD mice with spontaneous diabetes (BG >350 mg/dl for at least 1 week) can be transplanted under the renal capsule with 4 transgenic intermediate lobe pituitaries. This tissue dosage has been shown to reverse hyperglycemia (Lipes, M. A., Cooper, E. M., Skelly, R., Rhodes, C. J., Boschetti, E., Weir, G. C. & Davalli, A. M.: (1996) Proc. *Natl. Acad. Sci. USA* 93: 8595–8600). After transplantation, the bioengineered ILins grafts and (unmanipulated ILins control grafts), mice will be followed with overnight fasting and random blood glucose levels three times weekly using a One Touch meter (Lifescan) and measuring body weights. Transplanted mice will be followed for at least 6 months, or until hyperglycemia recurs. Perfusion experiments will be carried out to evaluate whether glucose-stimulated insulin secretion in grafts containing the bioengineered pituitary cells occurs in a time frame in vivo that resembles the rapid islet β-cell response.

Two weeks after transplantation, glucose levels can be studied under a variety of physiological conditions to determine whether normal or near normal glucose homeostasis is achieved and whether the pituitary-derived insulin is being regulated appropriately. Blood glucose regulation can be studied by glucose tolerance tests as we have described (Araki, E., Lipes, M. A., Patti, M. E., Bruning, J. C., Haag, B., Johnson, R. S. & Kahn, C. R.: (1994) *Nature* 372: 186–190). Transplanted mice can be fasted overnight and given an intraperitoneal (i.p.) injection of glucose, and bled at various times after injection to determine serum glucose and insulin levels. The glucose tolerance curves can be compared to glucose tolerance results in unmanipulated NOD mice.

Insulin secretion is also regulated by several other factors, including amino acids and certain pharmacological agents. An amino-acid infusion test with perfused kidney will be performed on fasting diabetic mice transplanted with the bioengineered ILins tissues or unmanipulated control ILins tissues. Insulin secretion responses are normally seen with 5 min of amino acid infusion and would be expected to decline gradually over the next 40 min (Selden et al, 1986). It will also be examined whether insulin secretion in the bioengineered ILins pituitary grafts responds to tolbutamide, a sulfonylurea derivative known to bind to specific receptors that are abundant in β cells and are present at lower levels in pituitary cells (Aguilar-Bryan et al., 1995). Within 20 min of an infusion of a solution containing 0.5 mg tolbutamide, insulin levels should peak, then rapidly decrease over the next 10 min (Selden, 1986).

Administration of GLP-1 prevents post-prandial glucose excursions in diabetic mice harboring insulin-producing IL pituitary grafts. To determine whether overexpression of the GLP-1R (to levels similar to islet β cells) improves sensitivity to physiological levels of GLP-1 that occur after eating, diabetic NOD mice harboring the genetically engineered ILins grafts can undergo meal tolerance tests in the absence of exogenously administered GLP-1. Blood glucose and insulin levels can be measured at the end of the fast and at serial time points after feeding.

Genetically modified insulin producing pituitaries of NOD transgenic mice should be tested to determine if they become targeted by the autoimmune process. To assess for the development of hypophysitis, the transgenic pituitaries can be serially analyzed for immune infiltration from 20 weeks of age (when insulitis is present in 100% of NOD mice) to the onset of diabetes. Bioengineered ILins grafts at the end of the transplant period can be analyzed for evidence of immune attack and to determine the levels of expression of insulin, POMC peptides and the introduced glucose sensors Example 20

Infection of Primary Cultures of ILins Cells with GLUT-2-containing Adenovirus Resulted in High Levels of GLUT-2 Protein Western blot analysis showed that treatment of IL cells with the AdCMV-GKB.1 virus resulted in large increases in glucokinase protein relative to Ad-CMV-LacZ infected control pituitary cells, as detected with sheep anti-rat glucokinase antiserum that was raised against the common regions of liver and islet glucokinase polypeptide. Although there was ~2-fold greater GLUT-2 expression in the transfected IL cells compared to liver, 50-fold more liver protein than IL protein was loaded (25 g vs. 0.5 g, respectively). Thus, high expression levels of GK and GLUT-2 in IL pituitary cells were obtained adenoviral gene delivery system.

Example 21

Expression of the Islet Isoform of Glucokinase in IL Cells Results in High Levels of Functional Glucokinase Enzymatic Activity The glucokinase encoding Ad-GK.B1 vector was evaluated by immunoblot and enzyme activity analysis. By Western blot analysis, treatment of IL cells with AdGK.B1 resulted in a marked increase in immunodetectable GK relative to IL cells treated with the AdCMV-βgal control virus.

GK activity could not be detected in primary untransfected or control AdCMV-β gal-transfected extracts of IL tissues. Similar findings have been reported for primary AL extracts and have been attributed to tissue-specific alternate RNA splicing events that disrupt the GK reading frame (Liang et al, 1991; Hughes et al., 1991). To investigate whether functional GK activity could be introduced into IL cells, primary cultures of ILins cells were infected with the Ad-GK.B1 vector at an MOI of 5× and 30×, respectively, or control AdCMV-βgal virus at an MOI of 10×. After 48 hours, lysates were prepared and glucose phosphorylating activity was measured by the fluorometric method (Trus et al., 1981; Liang et al., 1996). At 0.5 mM glucose, hexokinase activity in the adenovirus transduced IL cells was similar to parental IL tissue, varying from 1.54 to 2.81 nmol/h/g total protein. At >6 mM glucose, the IL cells treated with Ad-GK.B1 showed high levels of GK activity, which, importantly, correlated with increasing glucose concentration. The levels of functional GK activity were also correlated with the amount of virus introduced into the cells, with activity levels of 28 and 56 nmol/h/g total protein corresponding to MOIs of 5 and 30, respectively. These studies demonstrate that the islet isoform of GK was clearly active in GK.B1-IL pituitary cells treated with GK.B1-containing adenovirus with GK activity comprising >90% of the total glucose phosphorylating activity. See FIG. 9 and Table 1.

TABLE 1

Glucose phosphorylation in intermediate lobe (IL) cells

| Cell type | Total glucose phosphorylation (nmol/h/μg protein) | Glucokinase (nmol/h/μg protein) 60 mM glucose | Glucokinase, % of total |
| --- | --- | --- | --- |
| IL | | | |
| Parental | 1.7 | 0–0.15 | 0–8.8 |
| βgal | 1.68 | 0–0.2 | 0–11.9 |
| GK (MOI 5) | 27.27 | 24.71 | 90.6 |
| GK (MOI 30) | 54.31 | 51.5 | 94.8 |

It is possible that the high levels of endogenous hexokinase activity by IL cells may lower the threshold for glucose-stimulated insulin secretion in the bioengineered insulin-producing IL cells. If necessary, the high levels of hexokinase could be reduced by anti-sense or knockout approaches.

Example 22

Expression Ad-GK.B1 and Ad-GLUT-2 in IL Pituitary Cells has a Potent Enhancing Effect on Glucose Metabolism Glucokinase activity in transfected IL cells increased in proportion to the glucose concentration of the culture media. To determine the metabolic impact of these manipulations, the glucose concentration dependencies of glucose usage (as a readout for glucose metabolism) was examined in primary cultures of cells transfected with Ad-CMVGK.B1 and Ad-CMVGLUT-2 individually or together. Glucose usage was monitored by measuring the conversion 5-[$^3$H] and 2-[$^3$H] glucose (DuPont NEN) to $^3$H$_2$O, as described (Trus et al., 1981; Hughes et al., 1993) at 0.3, 3 mM and 20 mM glucose.

This is discussed in more detail below.

The expression of the islet isoform of glucokinase B.1 (GK.B1) and the high-capacity glucose transporter, GLUT-2, in primary cultures of pituitary cells conferred glucose-sensing capabilities to these cells within the physiologic glucose range. For these experiments, primary pituitary cultures were treated with recombinant adenoviruses containing either GK.B1 and/or the GLUT-2 gene. Transduction of each of these viruses into pituitary cells results in significant levels of glucokinase and GLUT-2 protein (as determined by Western blot analysis) which were associated with the introduction of functional GK and GLUT-2 activities. To determine whether either of these manipulations, individually or in combination, would confer glucose sensing capabilities, the conversion of 5-[$^3$H]glucose to $^3$H$_2$O at 0.3, 3, and 20 mM glucose was measured. As shown in FIG. 7, these studies demonstrated that the single transduction of primary cultures of pituitary cells with recombinant adenovirus containing either GLUT-2 or GK.B1 had minimal effects on the rates of [5-$^3$H]glucose metabolism, compared to control LacZ-infected cells. However, co-transduction of IL cells with both the GLUT-2- and GK-containing adenoviruses resulted in a marked increase in glucose responsivity over the range of glucose concentrations from 3 to 20 mM, with glucose usage increasing from 1.61±0.27 to 3.20±0.60 nmol/h/ig protein, respectively. By contrast, glucose usage in cells infected with the control LacZ-containing adenovirus remained essentially unchanged from 3 mM to 20 mM glucose, measuring 0.84±0.13 to 0.97±0.23 nmol/h/ig protein, respectively. These findings are the first to demonstrate that the co-expression of GLUT-2 and GK.B1 can confer glucose-sensing capabilities within the physiologic range in non-â cells. These results markedly differ from previously published studies, including those by Newgard and colleagues in which overexpression of GLUT-2 in glucokinase-expressing AtT-20ins cells was not associated with enhanced glucose metabolism over a full range of glucose concentrations from 10 iM to 20 mM.

Example 23

Generation of Transgenic Mice Expressing GK.B1 and GLUT2 in Insulin-producing IL Cells Transgenic founder mice that express GLUT2 and GK individually and together under the control of the POMC promoter were made. These constructs were microinjected into embryos from POMC-insulin transgenic mice. Three lines (36, 46, and 47) expressed both GLUT2 and GK.B1 transgenes. These founders can be bred to establish transgenic lines for further analysis. In an initial screening, IL pituitary lysates from one line (33) express similar levels of glucokinase activity to liver. The availability of transgenic animals will provide a valuable source of insulin-producing IL tissues in which virtually all the cells of interest express the transgenes of interest.

Those skilled in the art will recognize, or be able to ascertain using no more than routine experimentation, many equivalents to the specific embodiments and methods described herein. Such equivalents are intended to be encompassed by the scope of the following claims.

Example 24

Insulin-producing Intermediate Lobe Tissues are not Damaged by Pathogenic Insulin-specific T-cell Clones To more directly examine the resistance of insulin-producing IL tissues to immune attack, an adoptive transfer model system using the highly pathogenic insulin-specific, CD4+ T-cell clone PD12-4.4 was established. These T-cell clones, isolated from insulitis lesions of NOD mice are specific for insulin peptide B9–23 in the context of the NOD class II MHC (I-A$^g$). Streptozotocin-induced diabetic NOD scid mice (blood glucose [BG] levels >300 mg/dl) were transplanted under the opposite kidney capsules with equivalent amounts of insulin-producing tissues: i.e., 110 islets or insulin-producing IL tissue from 2 donors. This tissue combination resulted in normalization of BG levels (BG=103±25 mg/dl). When the transplanted NODscid mice received 2×10$^7$ cells from insulin-specific T-cell PD12-4.4 clones, severe hyperglycemia recurred. Although the islet grafts became heavily infiltrated with complete β-cell destruction, the IL grafts under the opposite kidney capsule were, in marked contrast, free of damage and had abundant insulin staining, with a similar appearance to the insulin-producing IL grafts of control mice that received saline. See FIG. 4A.

Example 25

Intermediate Lobe Tissues are Resistant to Allograft Rejection

Figure 4:
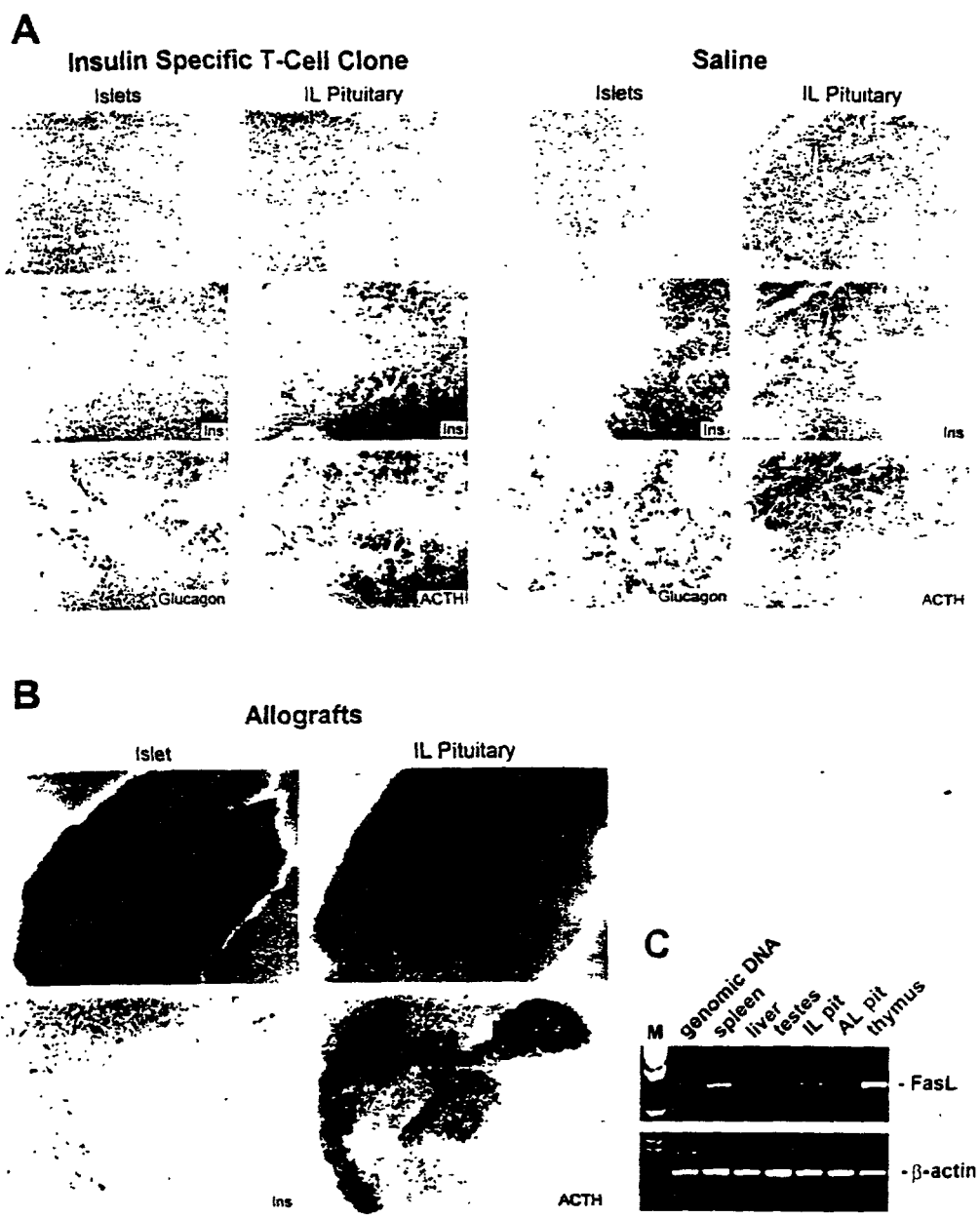
FIG. 4C is a gel which shows the expression of Fas ligand (FasL) and control β-actin in mRNA of various tissues from NOD mice by RT-PCR.
Figure 5:
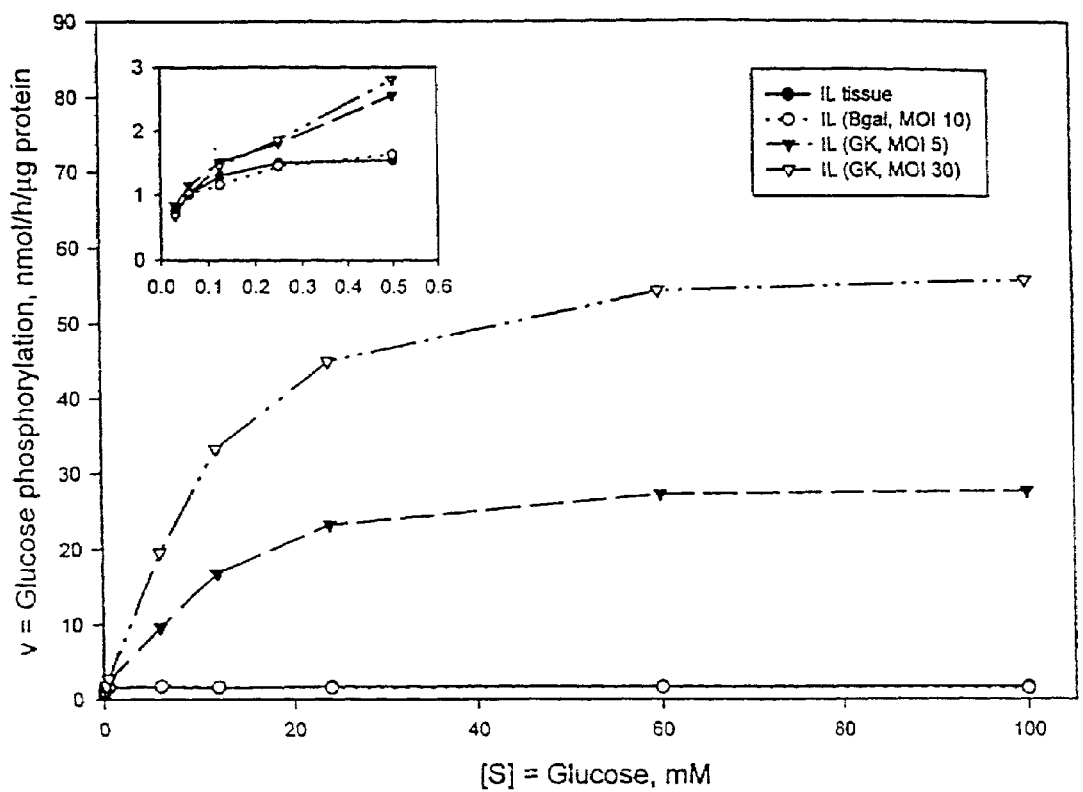
FIG. 5 is a depiction of glucose phosphorylation versus glucose concentration. Solid circles, IL tissue; open circles IL (βgal at an MOI of 10); solid triangles, IL (GK at an MOI of 5.0); open triangles, IL (GK at an MOI of 30).

In allograft experiments (C3H donors→BALB/c recipients), transplantation of islet allografts under the kidney capsule resulted in the development of severe necrosis (top left panel, view from stereomicroscope in FIG. 4B) and an intense inflammatory response, with little insulin-positive cells present by 21 days after transplantation (bottom left panel in FIG. 4B). In contrast, the IL pituitary allografts transplanted under the opposite kidney capsule appeared very well vascularized (top right panel, view from stereomicroscope in FIG. 4B) with minimal evidence of rejection and abundant ACTH-positive cells present (bottom right panel in FIG. 4B).

Example 26

Intermediate Lobe Tissues Constitutively Express Fas Ligand

To investigate features of IL tissues which could explain its ability to elude immune attack, the expression of Fas ligand in IL tissues was followed by RT-PCR analysis using intron-spanning primers and total RNA isolated from the IL pituitary and several other organs. These studies showed that, like testes, the IL expressed significant amounts of Fas ligand transcripts. See FIG. 4C.

---

The invention claimed is:

1. A method of producing and secreting insulin in a subject in vivo, the method comprising introducing into the subject an intermediate lobe pituitary cell that is capable of storing and secreting insulin and comprises a nucleic acid sequence encoding insulin, the nucleic acid sequence being operatively linked to a heterologous promoter that directs expression of the nucleic acid sequence in the intermediate lobe pituitary cell, thereby producing and secreting insulin in said subject.

2. The method of claim 1, wherein said intermediate lobe pituitary cell is an autologous cell.

3. The method of claim 1, wherein said subject is a human and the intermediate lobe pituitary cell is an autologous cell.

4. The method of claim 1, wherein said intermediate lobe pituitary cell is an allogeneic cell.

5. The method of claim 1, wherein said promoter is a pro-opiomelanocortin (POMC) promoter.

6. The method of claim 1, wherein said intermediate lobe pituitary cell is a fetal or post natal cell.

7. The method of claim 1, wherein said subject is a human.

8. The method of claim 1, wherein said intermediate lobe pituitary cell is a cultured cell.

9. The method of claim 8, wherein said cultured cell is a cultured human cell.

10. The method of claim 1, further comprising the step of administering an immunosuppressant to the subject.

* * * * *

SEQUENCE LISTING

<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: primer for PCR

<400> SEQUENCE: 1
caatcaaaag cttcagcaag caggaaggta c         31

<210> SEQ ID NO 2
<211> LENGTH: 33
<212> TYPE: DNA
<213> ORGANISM: Artificial Sequence
<220> FEATURE:
<223> OTHER INFORMATION: primer for PCR

<400> SEQUENCE: 2
gctgaagctt tttgattgta gcggatcact tag        33

<210> SEQ ID NO 3
<211> LENGTH: 22
<212> TYPE: DNA
<213> ORGANISM: Artificial Sequence
<220> FEATURE:
<223> OTHER INFORMATION: primer for PCR

<400> SEQUENCE: 3
tcgtgtagat aactacgata cg                    22

-continued

```
<210> SEQ ID NO 4
<211> LENGTH: 13
<212> TYPE: DNA
<213> ORGANISM: Artificial Sequence
<220> FEATURE:
<223> OTHER INFORMATION: primer for PCR

<400> SEQUENCE: 4
caaaaagctt cag                                                          13

<210> SEQ ID NO 5
<211> LENGTH: 13
<212> TYPE: DNA
<213> ORGANISM: Artificial Sequence
<220> FEATURE:
<223> OTHER INFORMATION: primer for PCR

<400> SEQUENCE: 5
caaaaaccat cag                                                          13

<210> SEQ ID NO 6
<211> LENGTH: 13
<212> TYPE: DNA
<213> ORGANISM: Artificial Sequence
<220> FEATURE:
<223> OTHER INFORMATION: primer for PCR

<400> SEQUENCE: 6
ctgaagcttt ttg                                                          13
```